United States Patent
Chu

(10) Patent No.: US 7,588,890 B2
(45) Date of Patent: Sep. 15, 2009

(54) DEVICE FOR EXTRACTING BIOLOGICAL MOLECULES FROM TISSUE SPECIMENS AND METHODS FOR PREPARING THE SAME

(76) Inventor: Wei-Sing Chu, 12503 Montclair Dr., Silver Spring, MD (US) 20904

( * ) Notice: Subject to any disclaimer, the term of this patent is extended or adjusted under 35 U.S.C. 154(b) by 521 days.

(21) Appl. No.: 11/106,511

(22) Filed: Apr. 15, 2005

(65) Prior Publication Data
US 2005/0233367 A1 Oct. 20, 2005

Related U.S. Application Data

(60) Provisional application No. 60/562,570, filed on Apr. 16, 2004.

(51) Int. Cl.
*C12Q 1/68* (2006.01)
(52) U.S. Cl. ............ 435/6; 435/40.52; 435/287.2; 359/398; 436/6
(58) Field of Classification Search .......... 435/40.52; 359/398; 436/6
See application file for complete search history.

(56) References Cited

U.S. PATENT DOCUMENTS

| | | | | |
|---|---|---|---|---|
| 5,273,905 A | * | 12/1993 | Muller et al. | 432/286.5 |
| 5,346,672 A | * | 9/1994 | Stapleton et al. | 422/102 |
| 5,910,288 A | * | 6/1999 | Schembri | 422/102 |
| 6,017,725 A | * | 1/2000 | Hoffmann et al. | 435/40.5 |
| 6,340,563 B1 | * | 1/2002 | Finkelstein et al. | 435/6 |
| 6,673,620 B1 | * | 1/2004 | Loeffler et al. | 436/46 |
| 2002/0009794 A1 | * | 1/2002 | Danenberg et al. | 435/270 |
| 2002/0192806 A1 | * | 12/2002 | Custance et al. | 435/286.5 |
| 2003/0044823 A1 | * | 3/2003 | Wolf et al. | 435/6 |
| 2003/0147132 A1 | * | 8/2003 | Behnsen et al. | 359/368 |

OTHER PUBLICATIONS

Chu et al. "A nondestructive molecule extraction method allowing morphological and molecular analyses using a single tissue section". Laboratory Investigation. vol. 85, pp. 1416-1428 (2005).*
Michel et al. "Liver Gene Expression Porfiles of Rats treated with Clofibric Aced: Comparison of Whole Liver and Lasert Capture Microdissected Liver". Technical Advance, American Journal of Pathology. vol. 163, No. 6, pp. 2191-2199. (Dec. 2003).*

* cited by examiner

*Primary Examiner*—William H Beisner
*Assistant Examiner*—Michael Hobbs
(74) *Attorney, Agent, or Firm*—Nianxiang Zou

(57) ABSTRACT

The present invention provides a non-destructive macromolecules extraction (NDME) device for extracting high quantity of biological molecules (including, but not limited to, proteins, DNA, and/or RNA) from tissue specimens (including, but not limited to, fresh or fixed tissue sections, homogenized tissues, and cell cultures), while preserving the morphology and antigenicity of the tissue. The device contains a base, a slide cover, and a thermal control device. The tissue specimen is placed onto the base. The slide cover is mounted to the base to form a space where an extraction solution can be added. The device optionally contains a chamber cover over the slide cover. The chamber cover and the slide cover forms a reaction chamber where a steam is infused to maintain the humidity of the tissue. The extraction solution contains a detergent. The present invention also provides a method for extracting the same.

18 Claims, 18 Drawing Sheets

DEVICE FOR EXTRACTING BIOLOGICAL MOLECULES FROM TISSUE SPECIMENS AND METHODS FOR PREPARING THE SAME

RELATED APPLICATION

The present application claims the priority of U.S. Provisional Application Ser. No. 60/562,570, filed on Apr. 16, 2004, which is herein incorporated by reference.

FILED OF THE INVENTION

The present invention relates to a non-destructive macromolecules extraction (hereinafter "NDME") device for extracting biological molecules, preferably proteins, DNA, and/or RNA, from tissue specimens, including, but not limited to, thin-section of frozen tissue or paraffin-embedded fixed tissue, a layer of homogenized tissue, and/or tissue cultures. The morphology of the tissue specimens is maintained without destruction after the completion of the extraction. The present invention also relates to methods for extracting biological molecules from thin-section of frozen tissue or paraffin-embedded fixed tissue (especially fixed with formalin), and for better preparing tissue specimen for pathological studies.

BACKGROUND OF THE INVENTION

As the human genome project nears completion, the focus of research is shifting to the immense tasks of identifying the structures, functions, and interactions of proteins produced by individual genes, and determining their roles in cancers and other diseases (Marte B. *Nature* 2003, 422 (Suppl.): 191-237; Liotta L et al., *Nat. Reviews* 2000, 1:40-56; Emmert-Buck et al., *Am J Pathol.* 2000, 156:1109-1115). Analysis of tissue proteins and mRNA transcripts is limited by the current technologies for preserving clinical specimens. Traditional formalin-fixed paraffin-embedded (FFPE) specimens provide superior morphology and easy long-term storage of clinical specimens. However, FFPE specimens are not always compatible with current molecular techniques due to suboptimal recovery of most macromolecules.

Because of these extraction problems, frozen tissue is preferred for molecular research. However, large scale processing and storage of frozen tissue are impractical and expensive. In the routine practice of pathology, the need for superior morphology provided by FFPE outweighs the need for molecular diagnosis. This situation becomes even more problematic with limited biopsies. Therefore, a method that could efficiently extract high quality proteins and nucleic acids in sufficient quantities to perform any number of molecular diagnostic methods while providing optimal morphology from FFPE tissue would provide the ideal solution to many of these problems.

All currently available molecule extraction methods require the homogenization or destruction of tissues, fixed or fresh, such that multiple specimens must be prepared for both molecular analysis and histological diagnosis (Clark et al., *J Histochem Cytochem* 1986, 34 (5):679-682; Conti et al., *J Histochem Cytochem* 1988, 36 (5):547-550; Ikeda et al. *J Histochem Cytochem* 1998, 46(3):397-403). It is extremely difficult to extract macromolecules from FFPE clinical specimens due to cross-linking between proteins and nucleic acids. Drs. Clark and Damjanov reported in 1986 that keratin proteins could only be extracted from placenta tissues frozen at −30° C., or fixed in Carnoy's solution, but not from formalin-fixed tissues (Clark et al., *J Histochem Cytochem* 1986, 34 (5):679-682). Proteins from tissues fixed in non-cross-linking fixatives, such as acetone, alcohol, or Carnoy's solution could be readily extracted, analyzed by SDS-PAGE Coomassie blue staining and immunoblotting (Gillespie et al., *Am J Pathol* 2002, 160(2):449-457; Shibutani et al., *Lab Invest.* 2000, 80(2):199-208). However, similar extraction from formalin-fixed tissues generated no detectable bands in Coomassie blue-stained gels and very low amounts of highly degraded bands detectable by polyclonal antibody (Conti et al., *J Histochem Cytochem* 1988, 36 (5):547-550). These observations led investigators to suspect that formalin-fixation may destroy macromolecules and may not preserve tissues as well as other non-cross-linking fixatives. In the early 1990s, several groups reported that DNA and RNA remained well preserved in FFPE and could be extracted for PCR amplification although the mRNA size would be substantially reduced (von Weizsacker et al., *Biochem. Biophys. Res. Commun.* 1991, 174:176-180; Neubauer et al., *Oncogene* 1992, 7:1019-1025; Krafft et al., *Nucleic Acids Res.* 1999, 27(22):4436-43). Only recently have researchers succeeded in developing protein extraction methods for FFPE tissues (Ikeda et al. *J Histochem Cytochem* 1998, 46(3):397-403; Izawa et al., *Oncol Rep.* 2002, 9(6):1313-1318; Murphy et al., *Am J Clin Pathol.* 2001, 116(1):135-42). However, these processes are destructive and require several hours, substantial amounts of tissues, and high salt concentrations in order to achieve satisfactory protein yields for SDS-PAGE analysis.

The present invention, to be presented in the following sections, overcomes these problems by providing a device and a simple, rapid, and non-destructive molecule extraction (NDME) method which not only can extract high quantity of proteins and nucleic acids from frozen or formalin-fixed paraffin-embedded tissue specimens, but also can maintain the integrity of the tissue morphology and antigenicity after the biological molecules are extracted, which are useful for histopathological studies. Over 500 tissue specimens were tested using this device and the NDME method. The NDME device and method have demonstrated at least the following three potential applications: 1) simultaneous proteomic, genomic studies and histological analysis, including H&E, IHC, and ISH for difficulty clinical cases; 2) performance of retrospective studies for various diseases, particularly those that have not been investigated, and 3) identification of relationships between levels of disease-perturbed proteins and response to drug therapy, ultimately allowing clinicians to not only provide a morphologic diagnosis, but to determine which therapy will yield the greatest response.

SUMMARY OF THE INVENTION

In one embodiment of the present invention, a non-destructive macromolecules extraction ("NDME") device for extracting biological molecules (such as proteins, DNA, and/or RNA) from a tissue specimen is provided. The NDME device contains (1) a base which has a top surface and a bottom surface; (2) a slide cover adapted to mount on the top surface of the base; and (3) a thermal control device adapted to be connected to the bottom surface of said base. A tissue specimen is placed on the top surface of the base.

The base is made by a material that is suitable for receiving tissue specimens. The preferred base is made of glass, such as a glass slide. The slide cover is preferred to have an inner surface which protrudes near the central portion of the slide cover. The top surface of the base and the inner surface of the slide cover form a space for retaining an extraction solution. The space is preferably shallow around the central portion, and deep around the surrounding portion between the top surface of the base and the inner surface of the slide cover. The slide cover has an opening at the central portion which allows for adding the extraction solution to the space between the top surface of the base and the inner surface of the slide cover. One or more lateral hole(s) are provided at the surrounding portion(s) of the slide cover. Optionally, the device further comprises a chamber cover to cover over the top of the slide cover.

Depending on the set temperatures, the thermal control device can be a heat block, a cool block, a thermocouple, an ultrasonic device, or a microwave device. The tissue specimen is a thin-section of a frozen tissue or a paraffin-embedded fixed tissue, a layer of homogenized tissue, a cell smear, microorganisms or cell culture. The tissue of the paraffin-embedded specimen is usually previously fixed with a fixative, which can be formalin, acetone, alcohol, or Carnoy's solution.

The extraction solution contains detergent. There are two preferred extraction solutions, one for protein/peptide extraction (i.e., NDME-PE solution), and one for nucleic acid extraction (i.e., NDME-NE solution). The NDME-PE solution contains water and sodium dodecyl sulfate (SDS) about 0.01% to 5% by weight, preferably at about 0.1% to 2% by weight, and most favorably at about 0.5% by weight of SDS. The NDME-NE solution contains detergent (such as Triton X-100), ethylenediaminetetraacetic acid (EDTA), and optionally citrate.

In another embodiment, a method for extracting biological molecules from a tissue specimen is provided. The method includes the following steps: (1) placing the tissue specimen onto the top surface of said base; (2) mounting the slide cover onto the top surface of the base to cover the tissue specimen; (3) adding the extraction solution (preferably in the range of about 5 µl to 250 µl, depending on the size of specimens) to the space between the top surface of the base and the inner surface of the slide cover; (4) connecting the thermal control device to the bottom surface of the base; (5) suing the thermal control device to adjust the tissue specimen to a desire temperature ; and (6) collecting the extraction solution which contains the biological molecules extracted from the tissue specimen.

Optionally, a chamber cover is adapted to cover over the slide cover after the temperature is adjusted by the thermal control device. The chamber cover is added for the convenience of infusing steam into the chamber in order to maintain the humidity of the tissue specimen during the extraction procedures.

The preferred temperature for extracting the biological molecules from the tissue specimen in the NDME method is can be in the range of −20° C. to 120° C. For frozen tissue, homogenized tissue or unfixed cell culture sample, lower temperature within this range is more suitable for the extraction, although the higher the temperature used, the shorter the period of time to be used for the extraction. The optimal time and temperature for the extraction in these tissue specimens are at about 4° C. to 100° C. for about 10-30 minutes. If extracted at 100° C., the extraction time should not exceed 5 minutes.

For the paraffin-embedded fixed tissue specimens, especially formalin-fixed paraffin-embedded ("FFPE") tissue specimens, the optimal temperature for the extraction is at the range of about 50° C. to 120° C., most favorably at about 100° C. The optimal time for extraction is about 5 minutes to 45 minutes.

For the thin-section of the frozen tissue or the paraffin-embedded fixed tissue, the tissue section is suitable for histopathological staining after the biological molecules are extracted because the NDME method does not destroy the integrity of the tissue morphology and antigenicity. To get success histopathological stains, it is important to avoid the section being dry during and after the extraction. After the remove of the extraction buffer from the specimen which is on the top surface of the base, the base with the specimen can be left in PBS solution.

(A) FFPE tonsil tissues were extracted using the following buffers: B=PE buffer from Bio-Quick (containing water and 0.5% SDS); X=NE buffer from Bio-Quick (containing phosphate buffer saline (PBS), 0.01 M citrate, 1 mM EDTA, 0.2% Triton X-100, and RNA inhibitors); E=0.01 M EDTA; C=10 mM citrate, P=Tissue-PE LB from Geno Tech.; and M=low-range protein mass marker. Right composite: Coomassie blue staining; Left composite:Silver staining.

(B) Lymph node tissues were extracted using PE buffer: 1=fresh, 2=routine-fixed FFPE, 3=over-fixed FFPE.

(C) Different tissues were extracted using PE buffers: Ln=lymph node, Lv=liver, Bn=brain, Lu=lung, and Pro=prostate.

Figure 5:
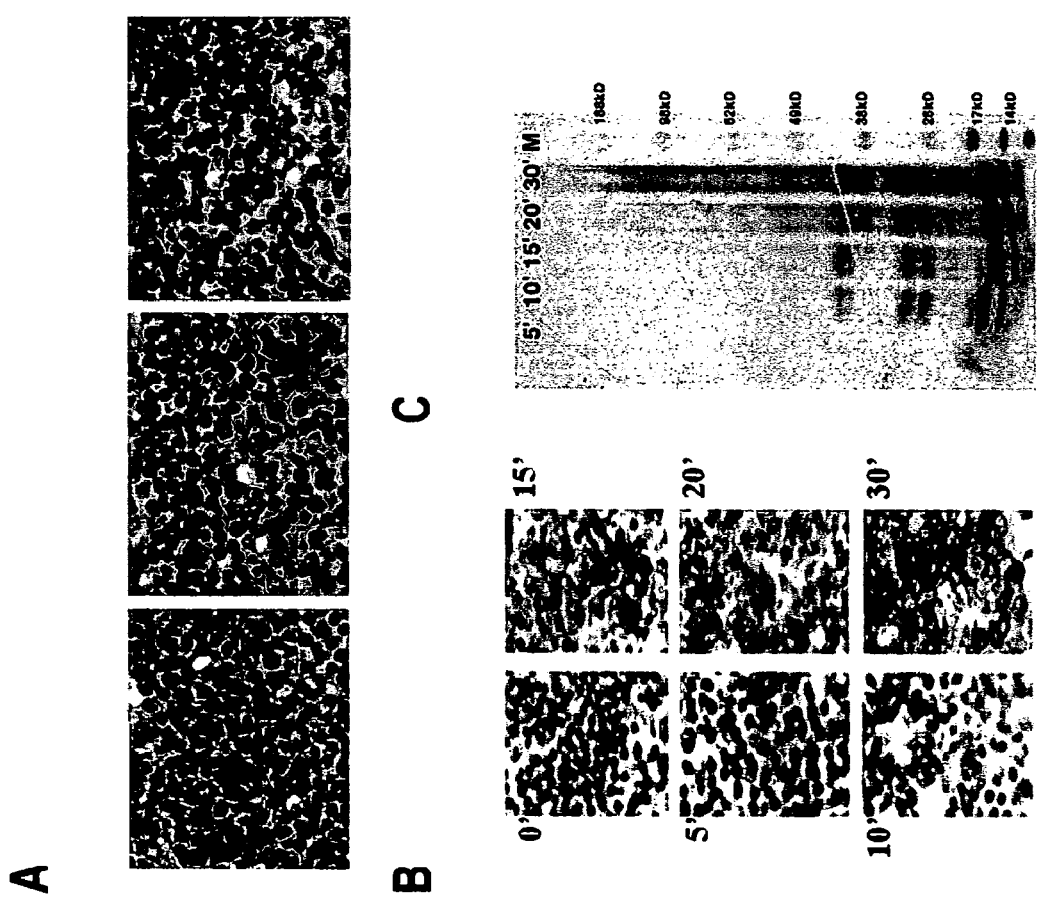

FIG. 5 shows non-destructive effects of the NDME method on preserving the tissue morphology after high quantity of proteins were extracted from the tissue:

(A) H&E staining of lymph node tissue sections: FFPE tissue section without the NDME treatment (left composite), FFPE tissue section with the NDME treatment (center composite), and frozen tissue section with the NDME treatment (right composite). The results show that 20 minutes of the NDME treatment on FFPE tissue section and 5 minutes of the NDME treatment on frozen tissue section did not alter the morphology of the tissue sections (1,000×).

(B) Immunohistochemical (IHC) staining against CD5 (400×) on FFPE lymph node tissue sections with the NDME treatment using PE buffer for 0, 5, 10, 15, 20, and 30 minutes, respectively. The results show that extended NDMB treatment brightened the IHC signal at a price of increased morphological damage.

(C) Extracts from FIG. 5B were analyzed by SDS-PAGE and stained with Coomassie blue. The results show that extended NDMB treatment generated more proteins.

Figure 6:
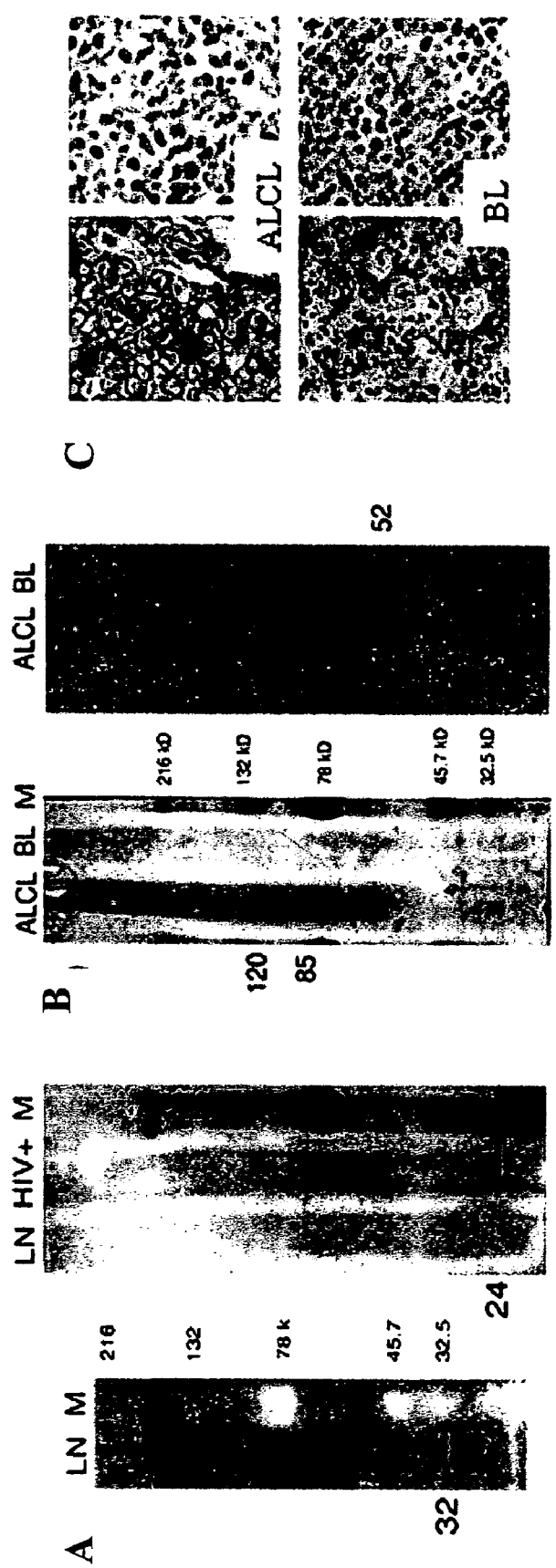

FIG. 6 shows protein (A and B) and morphological (C) analysis of FFPE lymph node tissues from patients with AIDS and various lymphomas with the NDMB treatment: LN=reactive lymph node; M=molecular markers; HIV+ =HIV+AIDS lymph node; ALCL=anaplastic large cell lymphoma; and BL=Burkitt's lymphoma.

(A) and (B) are Western blot of extracts from FFPE tissue sections after the NDME treatment and interacted with anti-CD20 (A, left panel, membrane glycoprotein), anti-HIV p24 (A, right panel, viral capsid protein), anti-CD30 (B, left panel, Golgi precursor protein), and anti-cyclin E (B, right panel, nuclear protein). Protein was extracted and analyzed on a 4-15% gradient SDS-PAGE gel, transferred onto PVDF.

(C) IHC of the ALCL (upper left and upper right panels) and BL (lower left and lower right panels) tissue sections (200×, as in Panel B) after the NDME treatment, showing that ALCL and BL were positive for cyclin E (upper and lower right panels), but only ALCL showed positive CD30 expression (upper left panel).

Figure 7:
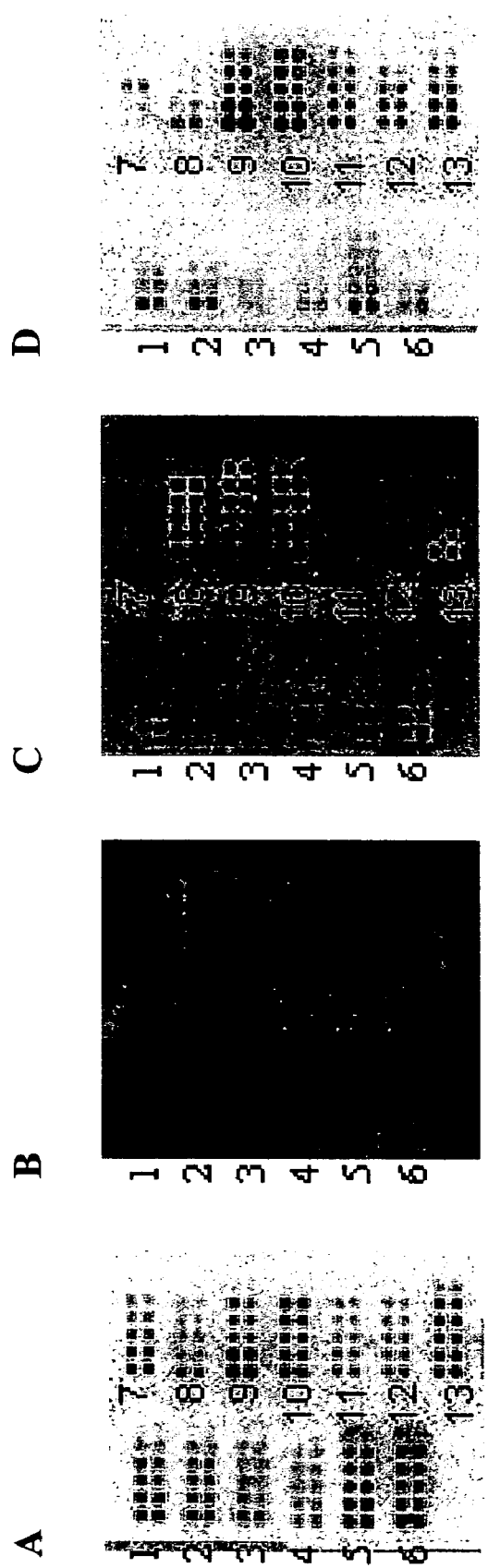

FIG. 7 shows the detection of proteins by reverse-phase protein array using sequential 2-fold dilutions of the NDME extracts from frozen, ethanol-fixed, and formalin-fixed tissue sections: 1=frozen lymph node (LN); 2=formalin-fixed LN; 3=ethanol-fixed LN; 4-6=formalin-fixed kidney; 7=formalin-fixed spleen; 8-10=formalin-fixed prostate; 11-12=formalin-fixed breast; and 13=formalin-fixed lung. Total proteins were stained with Sypro Ruby. Reaction with antibodies against PAP (B), PSA (C), or keratin (D) demonstrates protein expression level in different tissues. (A) shows total protein.

Figure 8:
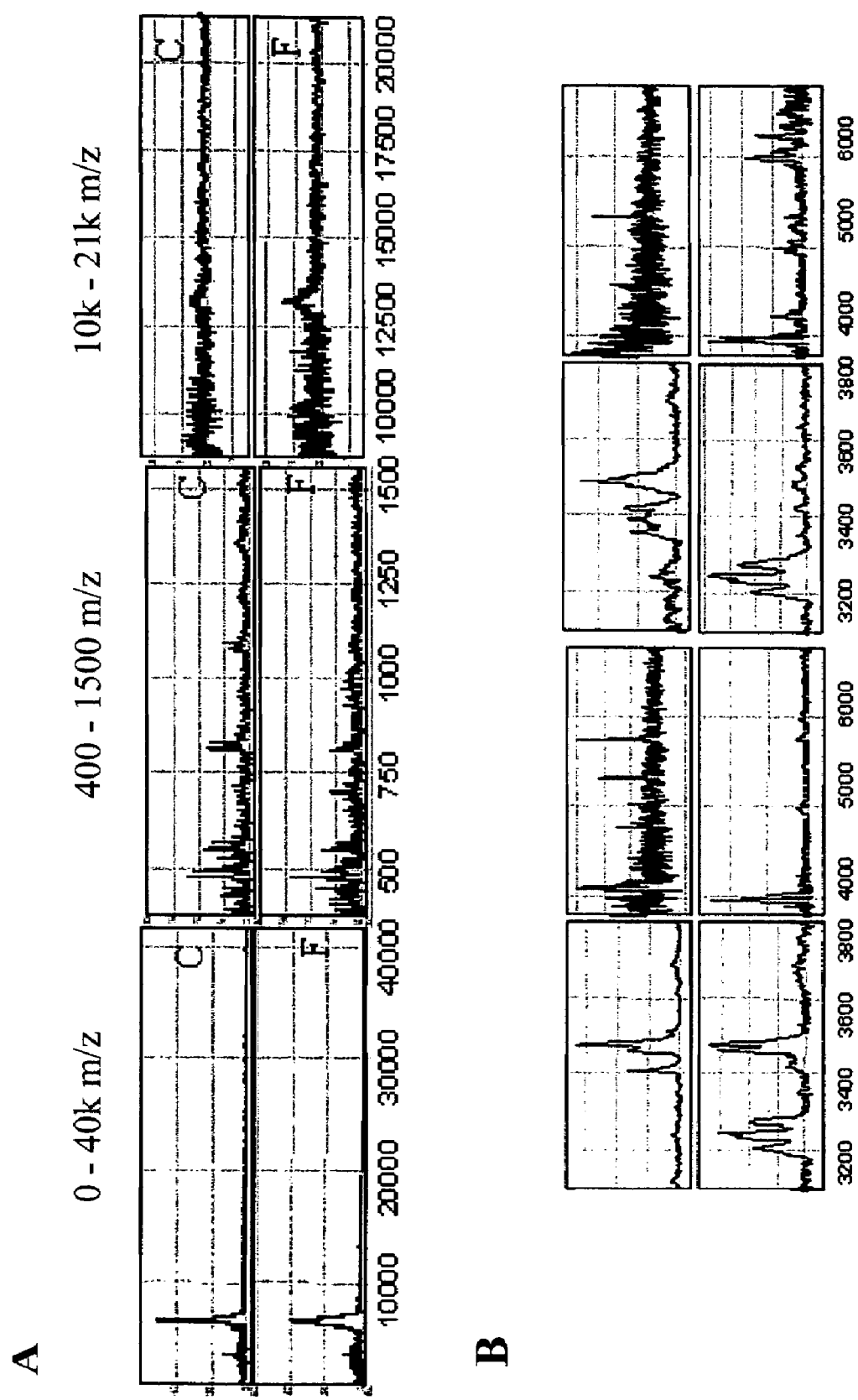

FIG. 8 shows that the NDME technology supports protein profiling by SELDI-TOF MS.

(A) Proteins extracted by NDME-PE were selected with a hydrophobic reverse phase protein chip and analyzed with PBS-II SELDI-TOF MS with software provided by the manufacturer: full range, 0-40 k m/z (left penal); 400-1500 m/z (center panel); 10 k-21 k m/z (right panel). C: Frozen tissue section. F: FFPE tissue section. Protein profiles of FFPE tissue resemble those of fresh tissue.

(B) Protein profiles of frozen (the 4 left panels) verses formalin fixed (the 4 right panels) pancreas sections were greatly affected by tissue fixation methods and the extraction buffers used (NDME-PE buffer, top 4 panels; NDME-U buffer, bottom 4 panels).

Figure 9:
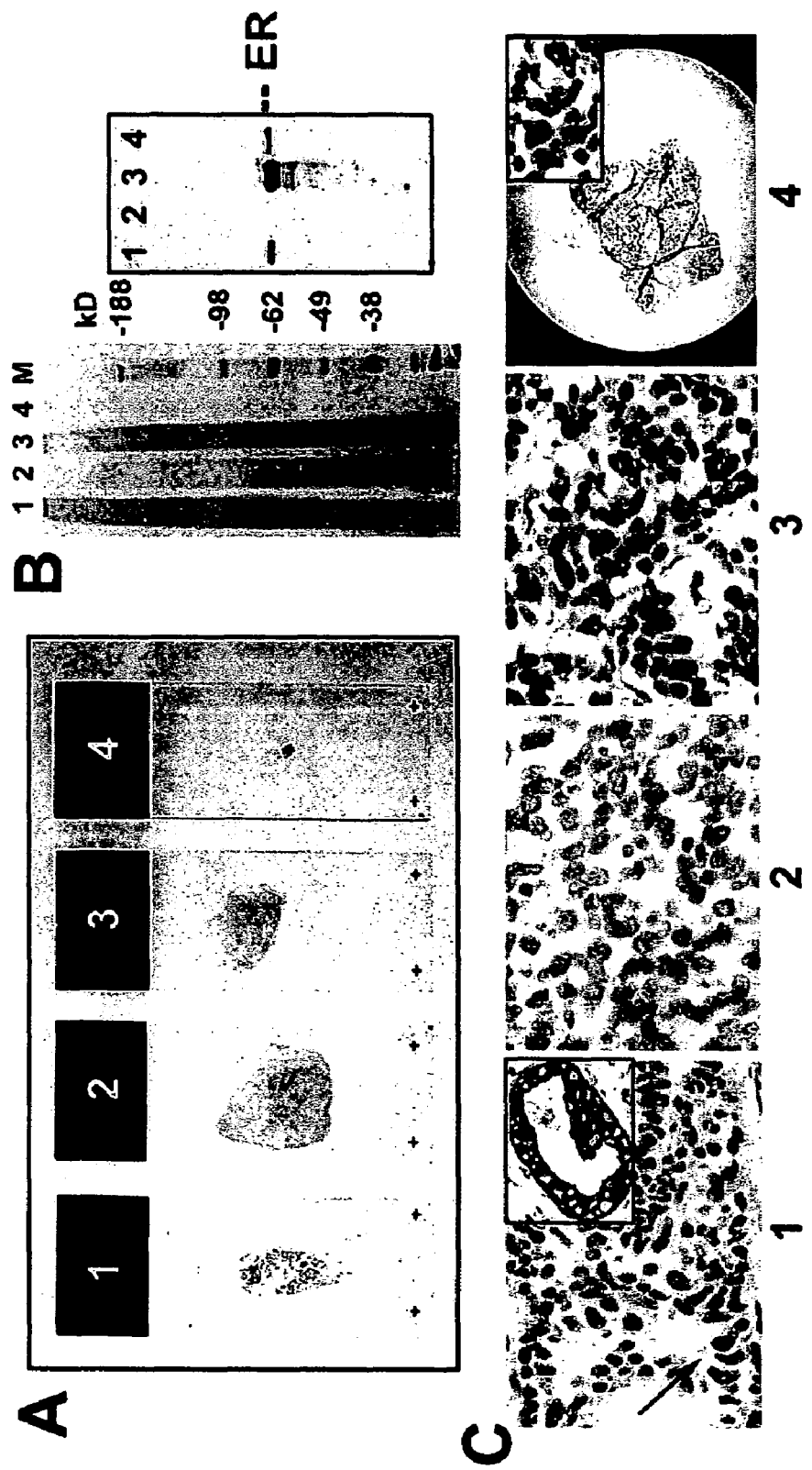

FIG. 9 shows the tissue sections on the microscopic glass slides (A), protein profiles in SDS-PAGE (B), and IHC staining of the tissue sections after the NDME treatment:

(A) shows that the tissue sections were left on the slides after the NDME extraction was completed. Slide 1=Her-2(+) and ER(−) breast carcinoma; Slide 2=ER(−) endometrial stromal sarcoma; Slide 3=ER(+) breast carcinoma; Slide 4=dissection of ER(+) breast carcinoma (~1.5×2 mm$^2$);

(B) shows the results of SDS-PAGE for total proteins (Left Panel) and ER specific protein (Right Panel) in the NDME extracts; and (C) shows IFC with anti-ER antibody on tissue sections of Slides 1 to 4 as shown in (A) after the NDME treatment. The arrow in C1 indicates one residue of the ER(+) benign gland. The inset in C1 is IHC with anti-Her-2 antibody. C4: microscopic view of the section 4 under 20× and 400× magnification.

Figure 10:
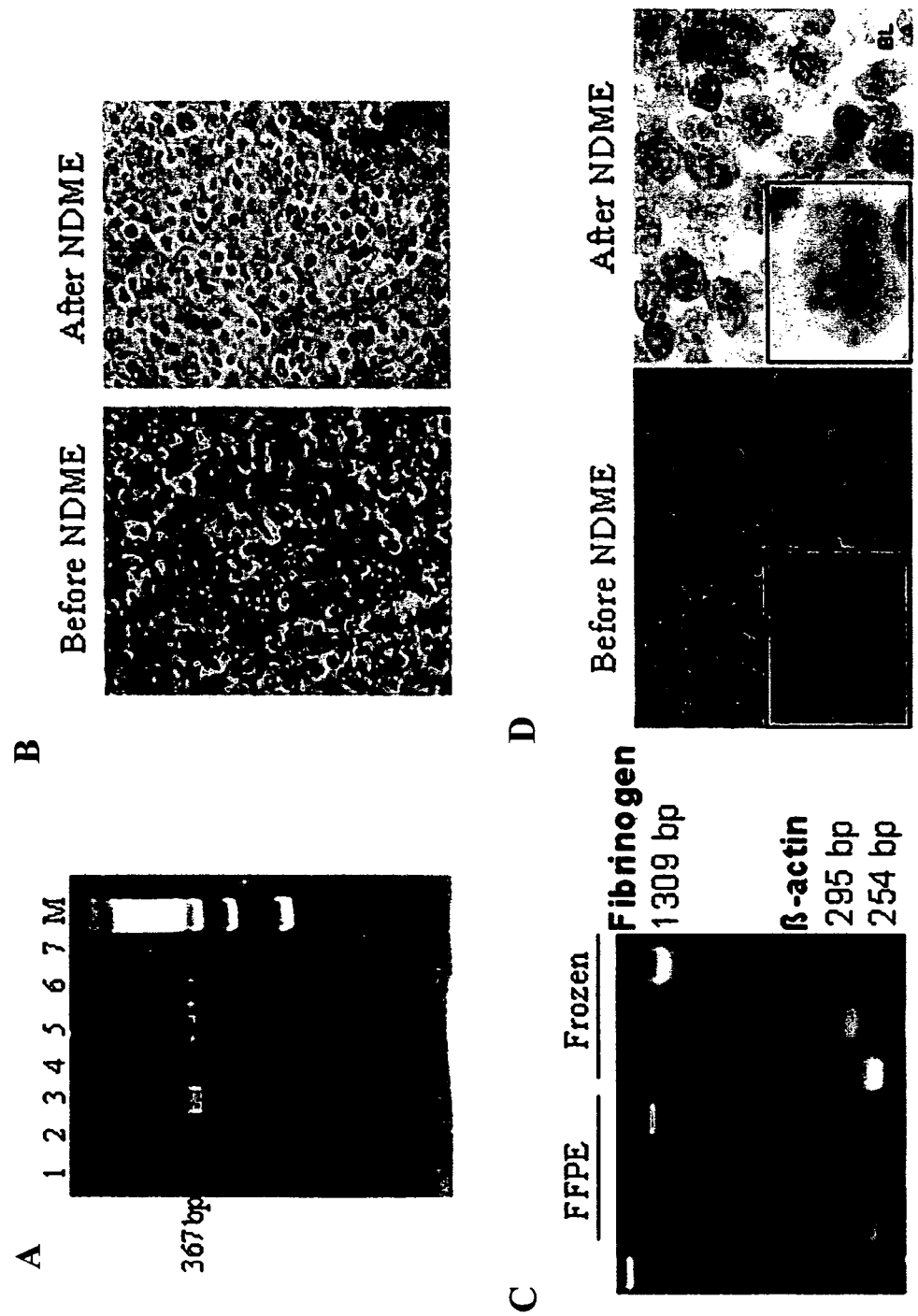

FIG. 10 shows that the NDME technology has the capacity of extracting RNA from 30-year-old archived FFPE retinal sample as demonstrated by the appearance of the 300 base pair product (A), microscopic detecting Epstein-Barr virus (RNA virus, demonstrated as black dots) in lymph node tissue section of patients with infectious mononucleosis (B), extracting DNA from FFPE and frozen tissue sections by the appearance of a band of 1,300 base pair (C), and microscopic detecting chromosome translocation (i.e., c-Myc translocation, demonstrated as separated green and red dot in a cell) in Burkitt's lymphoma tissue sections (D):

(A) RNA was extracted from 30-year-old archived FFPE retinal sections, generating amplicons of over 300 base pair (bp). RT-PCR amplification was performed using tissue extracts from 6 different retinal samples (lanes 1-6) in FFPE-NE buffer, followed by DNase treatment with primers for actin protein of 367 bp. M=100 bp DNA ladder.

(B) RNA-ISH of consecutive sections of lymph node with infectious mononucleosis (200×). The blue staining shows the results of Epstein-Barr virus early RNA (EBER) hybridization before and after NDME treatment.

(C) PCR of NDME extracts from FFPE and frozen tissue sections generated DNA fragments of over 1,300 bp.

(D) CISH detection of the c-Myc translocation (1,000×) in Burkitt's lymphoma tissue sections before and after NDME treatment.

Figure 11:
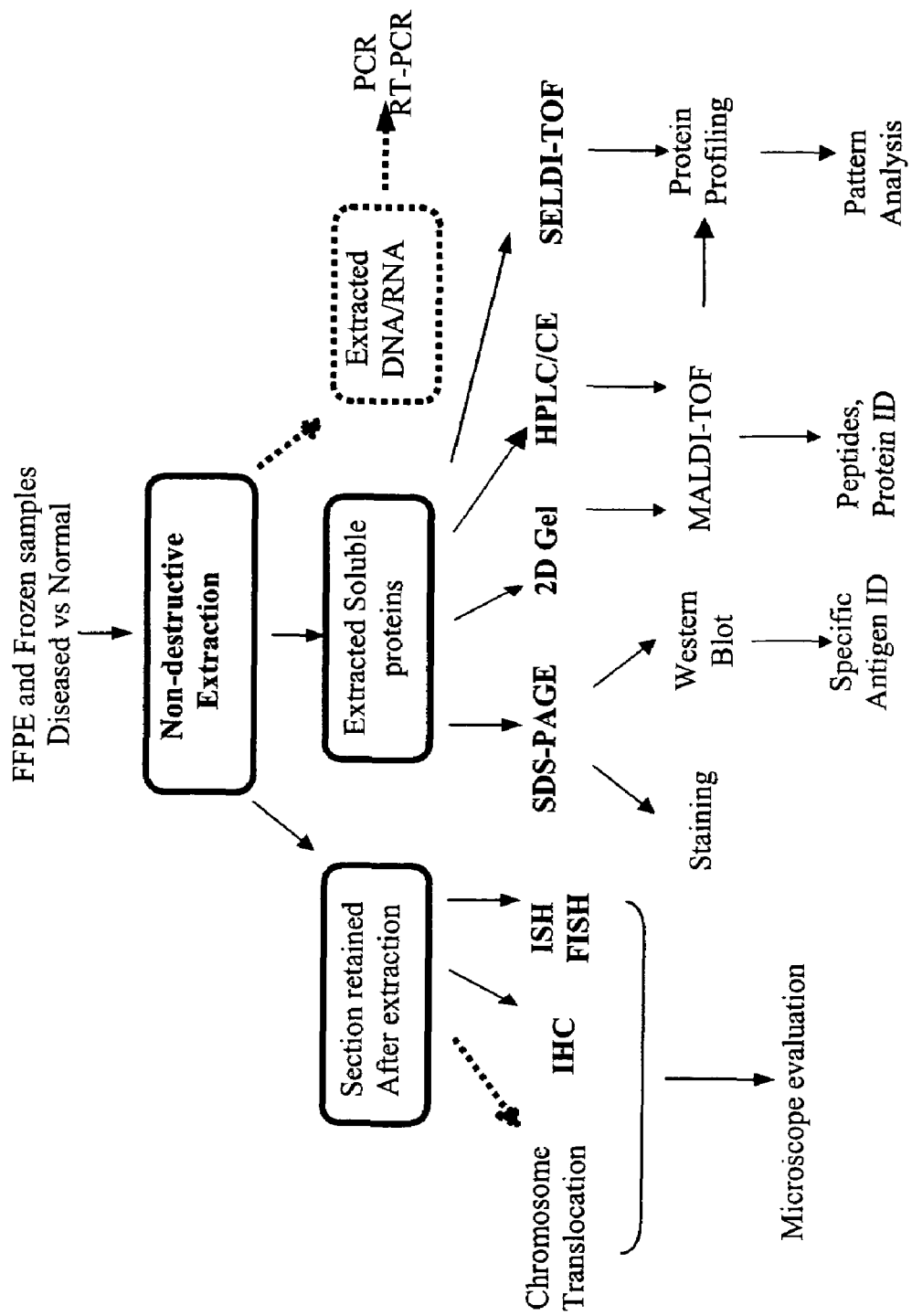

FIG. 11 shows a schematic diagram of potential applications in clinical diagnosis and bio-molecular analysis supported by the NDME system. Using a single tissue section (i.e., both FFPE and frozen samples), the extract from the NDME-procedures contain proteins, DNA, and RNA. The extract can be useful for downstream protein-oriented analysis such as by SDS-PAGE, 2D-gel, HPLC/CE, SELDI-TOF, and protein chips. The extracted DNA/RNA can be useful for downstream genomic studies by PCR, RT-PCR cDNA array techniques. The same tissue section after NDME treatment can be flurther examined using histopathological techniques, such as chromosome translocation, IHC, and ISH-FISH. In this way, NDME provides a useful tool to provide both molecular information and the localization information on a single specimen.

Figure 12:
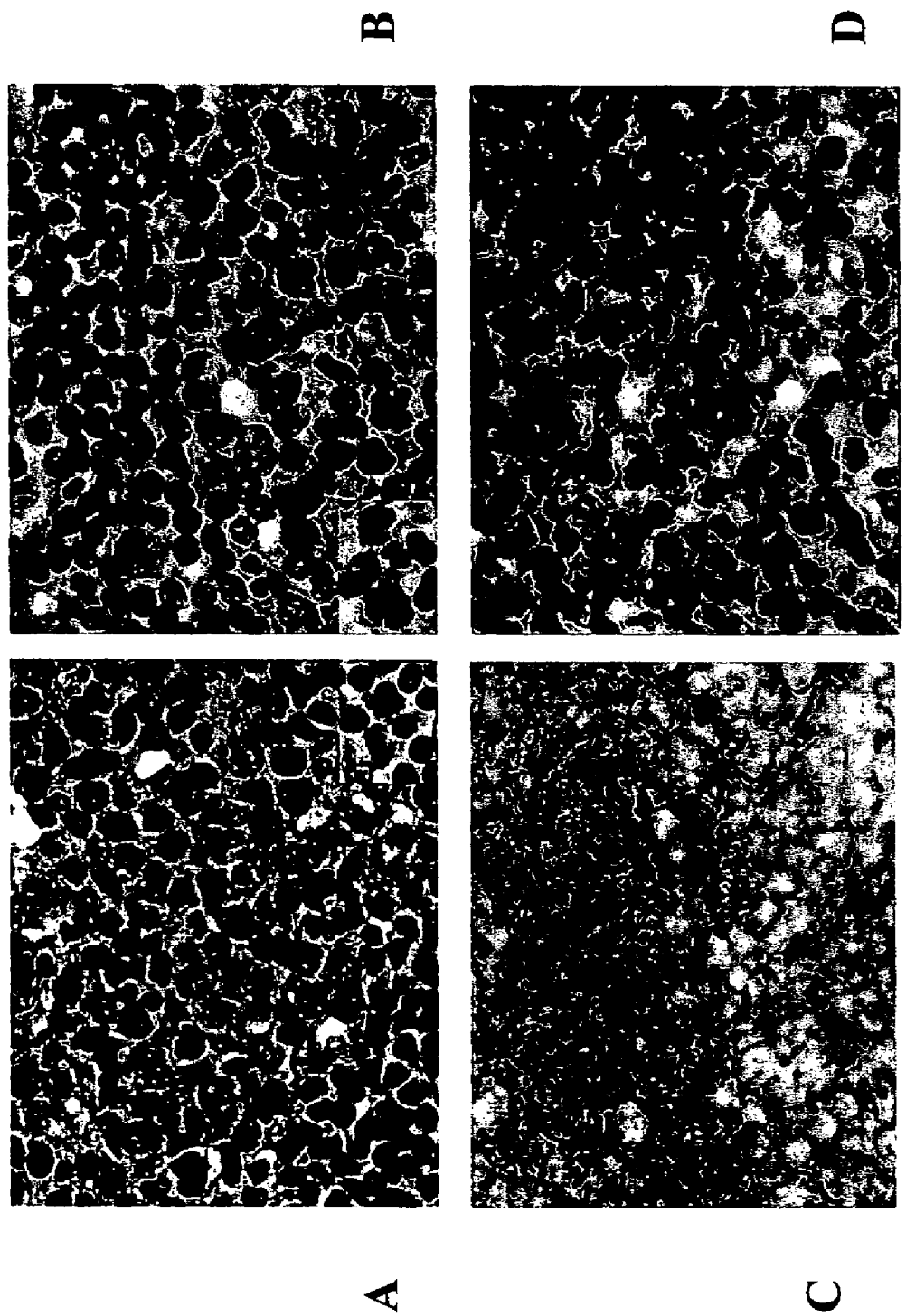

FIG. 12 shows the non-destructive morphological effects of the NDME method on the H&E and IHC staining of FFPE and frozen tissue sections: FFPE tissue sections untreated (A)

and treated with the NDME method (B); frozen tissue sections untreated (C) and treated with the NDME method (D). The results show that the NDME method not only did not destroy the morphology of the tissue section, but also enhance the resolution of the staining.

Figure 13:
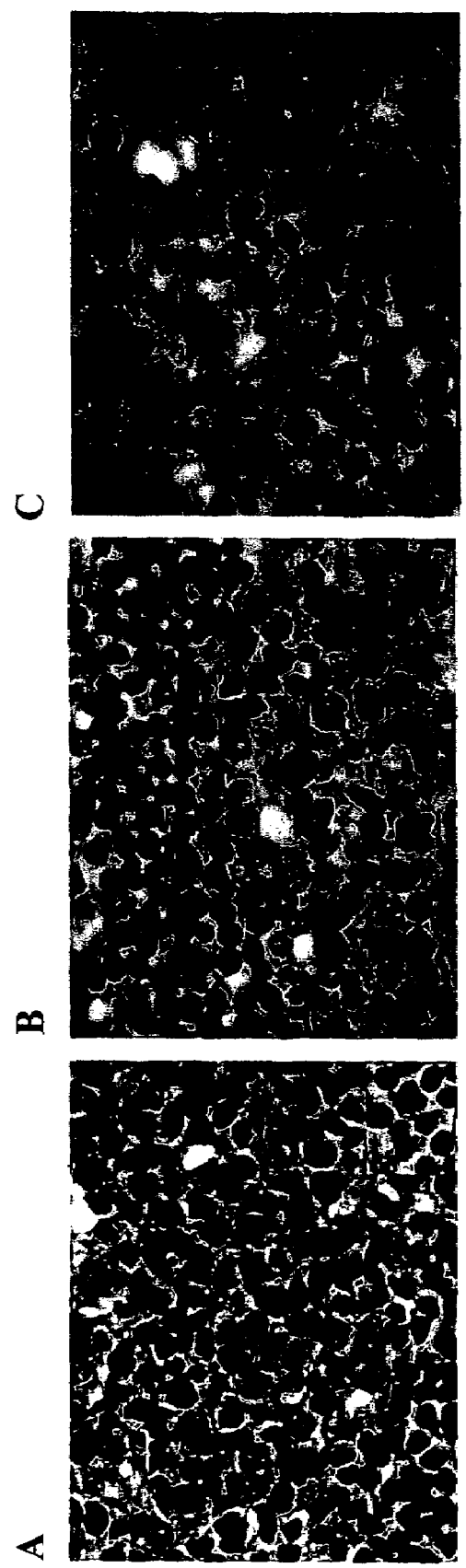

FIG. 13 shows the effects of different NDME buffers on the H&E staining of FFPE tissue sections: (A) untreated; (B) extracted with NDME-NE buffer (containing phosphate buffer saline (PBS), 0.01 M citrate, 1 mM EDTA, 0.2% Triton X-100, and RNA inhibitors); and (C) extracted with NDME-PE buffer (containing water and 0.5% SDS).

Figure 14:
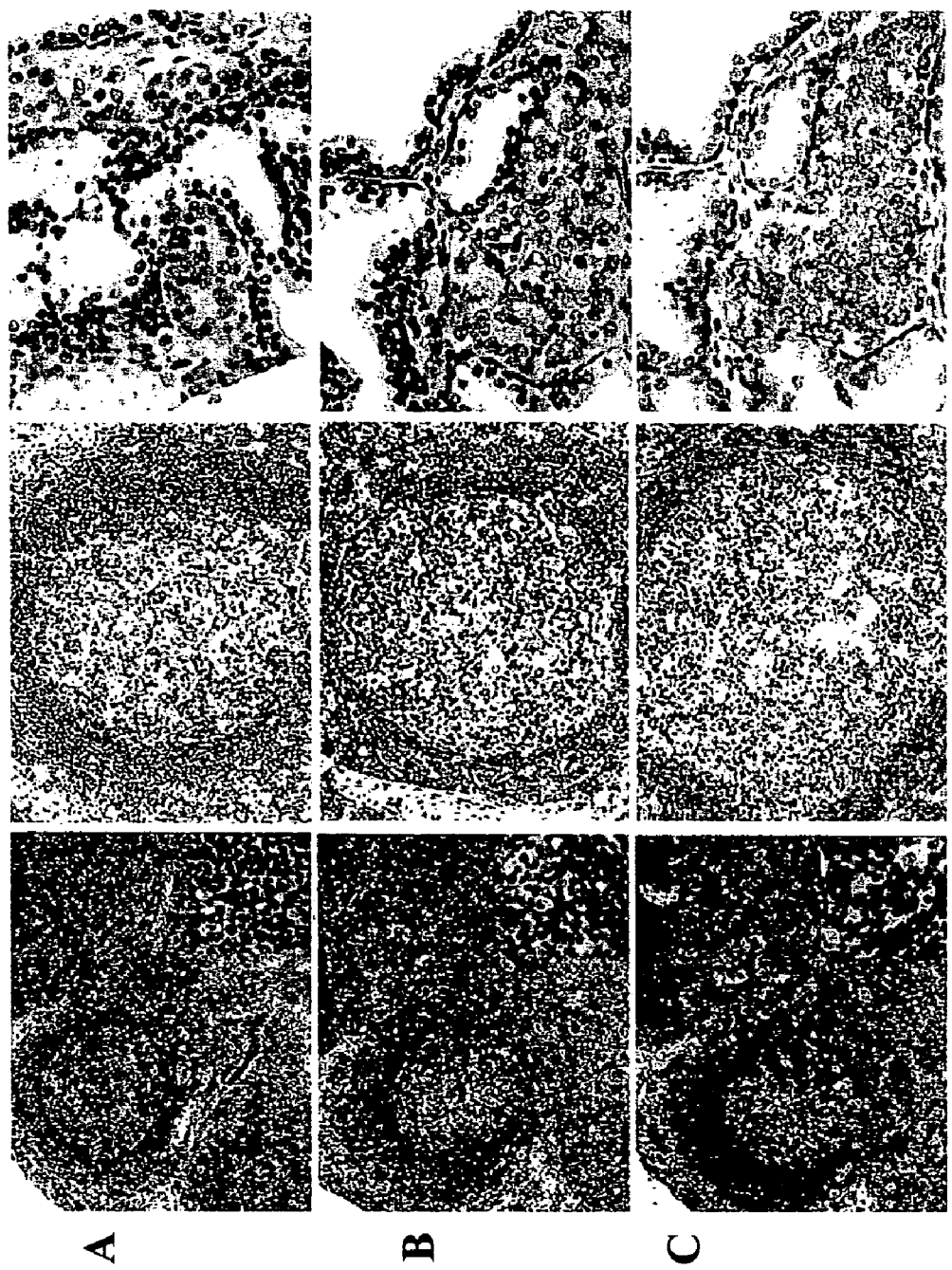

FIG. 14 shows the effects of different NDME buffers on the morphology and antigenicity of tissue sections: (A) tissue sections without the NDME treatment; (B) tissue sections treated with the NDME-NE buffer; and (C) tissue sections treated with the NDME-PE buffer. H & E staining (Left Panels); IHC staining with Bcl-6 antigen (Center Panels); and IHC staining with AMACR antigen (Right Panels).

Figure 15:
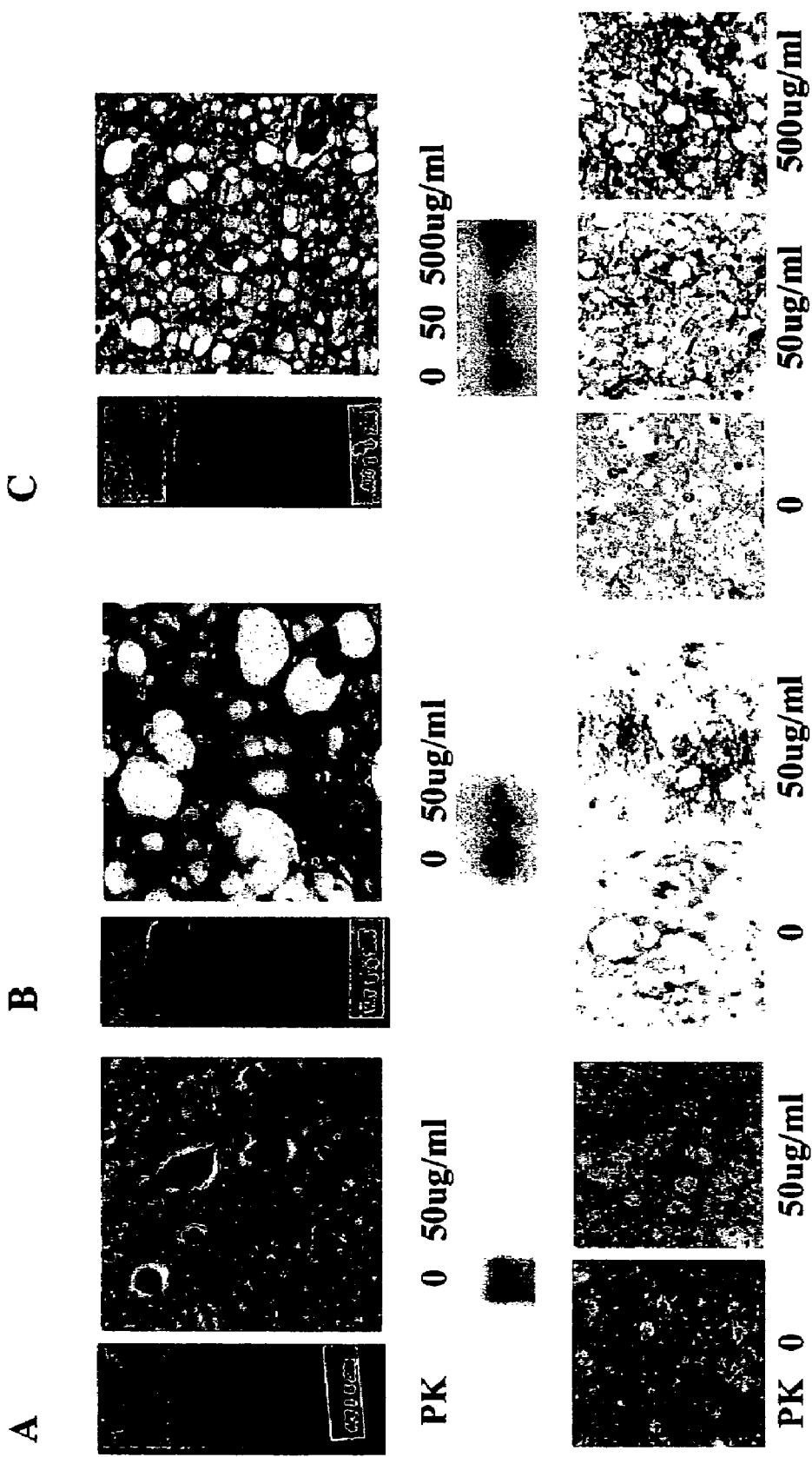

FIG. 15 shows the results of morphologic and proteomic analyses of brain tissue sections of normal brain (A), prion case I (B) and prion case II (C) after treatment with the NDME technology. The upper panels show the tissue sections on the tissue slide and the H&E morphologic results. The middle panels show the results of Western blotting that NDME extracted PrP protein detected by specific prion antibody (3F4) in prion case I and II but not in normal brain after proteinase K digestion. The bottom panels show the results of IHC that tissue sections after proteinase K digestion and NDME treatment are still able to stain by 3F4 antibody in prion case I and II but not in normal brain section.

Figure 16:
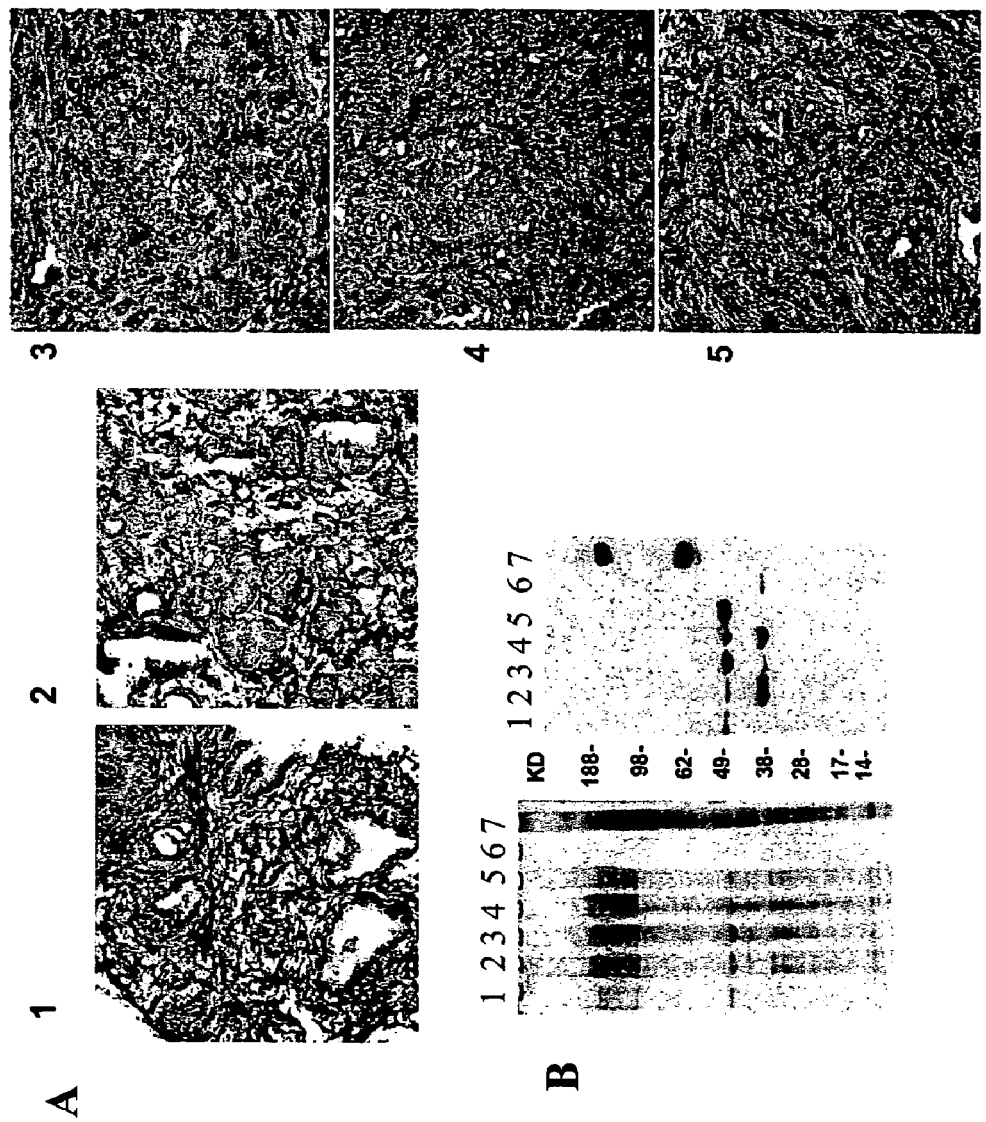

FIG. 16 shows the histologic and protein analysis results of prostate cancer frozen samples after NDME treatment. (A) shows corresponding H&E staining of the 5 regions from 4 specimens. (B) shows the SDS-PAGE by Coomassie blue staining of total proteins and Western blot by anti-AMACR pAb from Abcam. 1 & 2=benign and cancerous regions from the same tissue, respectively; 3-5=prostate cancer tissues, and 6 & 7=extracts from cell lines LNCap and 293, respectively.

Figure 17:
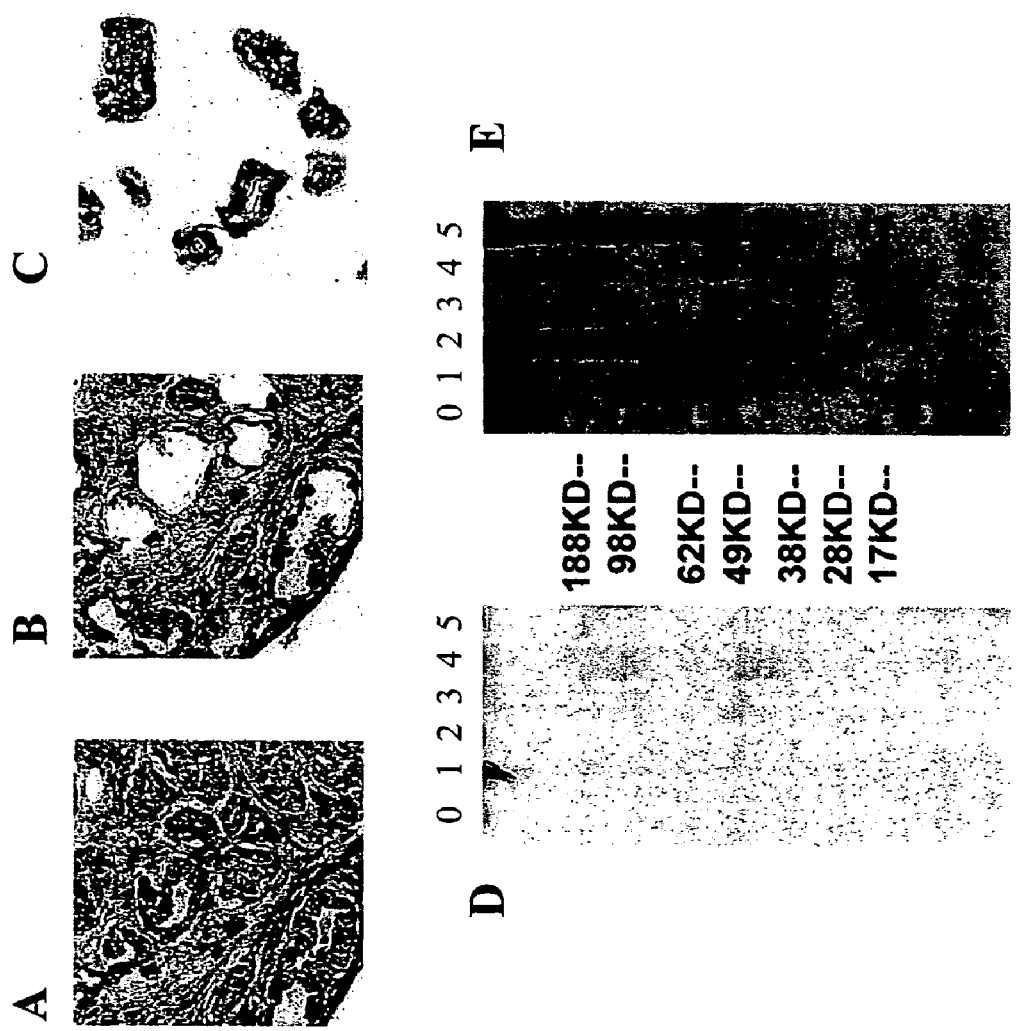

FIG. 17 shows NDME results of FFPE prostate cancer LCM samples. (A) shows the FFPE section sample before LCM. (B) shows the FFPE samples after LCM. (C) shows the samples remained on slide/cap. (D) shows the SDS-PAGE results. (E) shows the Western Blot with anti-AMACR. 1=case 326T, 2=case 320T, 3=case 430T, 4=case 488T, 5=case 564T.

Figure 18:
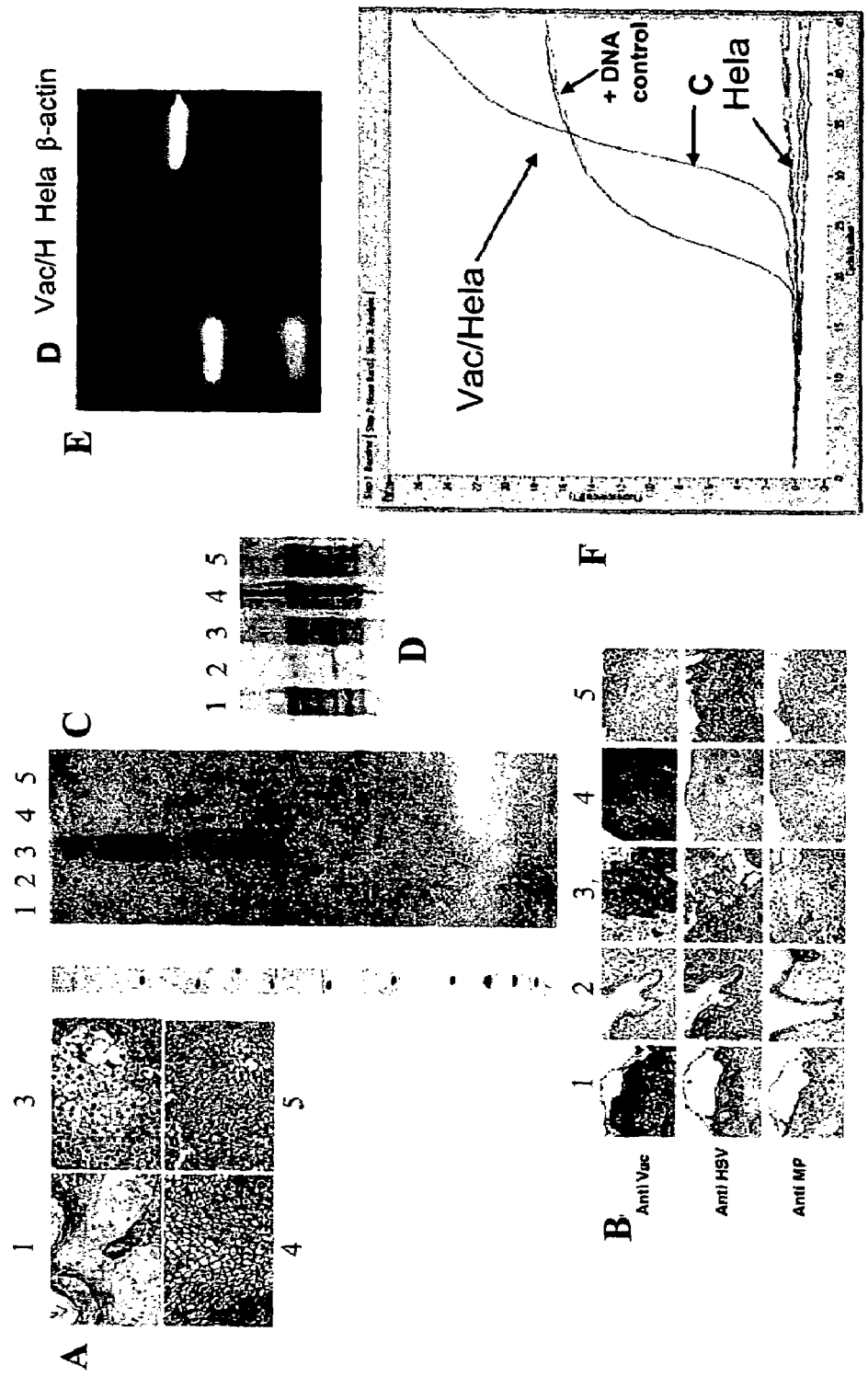

FIG. 18 shows NDME study of 50-years old tissue sections from smallpox patient, where 1 & 4=50-years old tissue sections; 2=normal skin; 3=positive control, vaccinia-infected tissue; 5=positive control, herpes simplex virus-infected tissue. (A) shows H&E staining (B) shows the results of IHC after NDME treatment; (C) shows the results of Western blotting with anti-Vac antibody that it binds a single 65 kD protein in smallpox-infected tissue (case 1 and 4) NDME extract but a major 200 kD protein and a minor 65 kD protein in generalized vaccinia-infected tissue (case 3) NDME extract; (D) shows the results of Western blotting with anti-pan keratin antibody AE1/AE3 that only reacts with difference isoform of keratins as housekeeping proteins; (E) shows that PCR products corresponding to the orthopoxvirus hemagglutinin gene products of 209 bp was amplified from the smallpox tissue (D=case 4) NDME extract; and (F) shows that Real-time PCR products corresponding to the vaccina hemagglutinin gene product was amplified from the vaccinia-infected tissue (C=case 3) NDME extract.

DETAILED DESCRIPTION OF THE INVENTION

The present invention provides a non-destructive macromolecules extraction (NDME) device and method for extracting macromolecules from a tissue specimen without destroying the tissue morphology. A tissue specimen includes, but is not limited to, tissue (fresh or fixed) and tissue sections, a cell smear, cells, cell culture and microorganisms. The NDME technology aims at reversing the formalin cross-linked proteins in fixed tissues to as closely as their natural, unfixed status under optimal reverse processing conditions. The NDMB technology not only can extract soluble proteins from FFPE/frozen tissue sections, but also is capable of maintaining the integrity of tissue structure morphology and retrieval of antigenicity after the extraction. The NDME technology can also be applied to cell smears, samples of cells, microorganisms, cell cultures. This technology allows proteomic as well as genomic studies using this rapid, non-destructive extraction method. In addition, the slide can be evaluated both before and after extraction for all current pathological diagnosis, including IHC, in situ hybridization (ISH), ISH-PCR, ISH-RT-PCR, and chromosome translocation (See e.g., FIG. 12).

Figure 1:
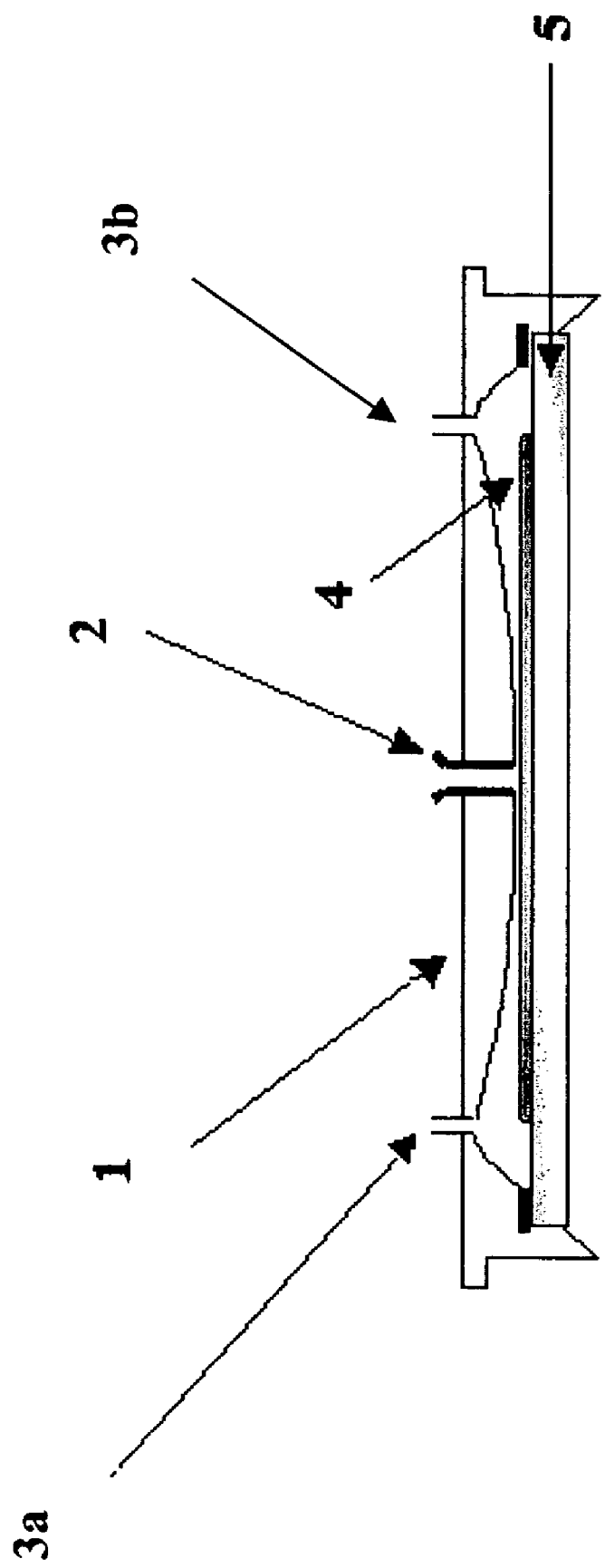
FIG. 1 is a cross-section of a front view of the slide cover (1) and base (5) of a preferred embodiment of the NDME device. The slide cover (1) has a central opening (2) and a pair of lateral holes (3a, 3b). A tissue specimen (4), which can be a frozen section, a formalin-fixed paraffin-embedded tissue section, a homogenized tissue, or a cell culture, is laid on top of the base (5).
Figure 2:
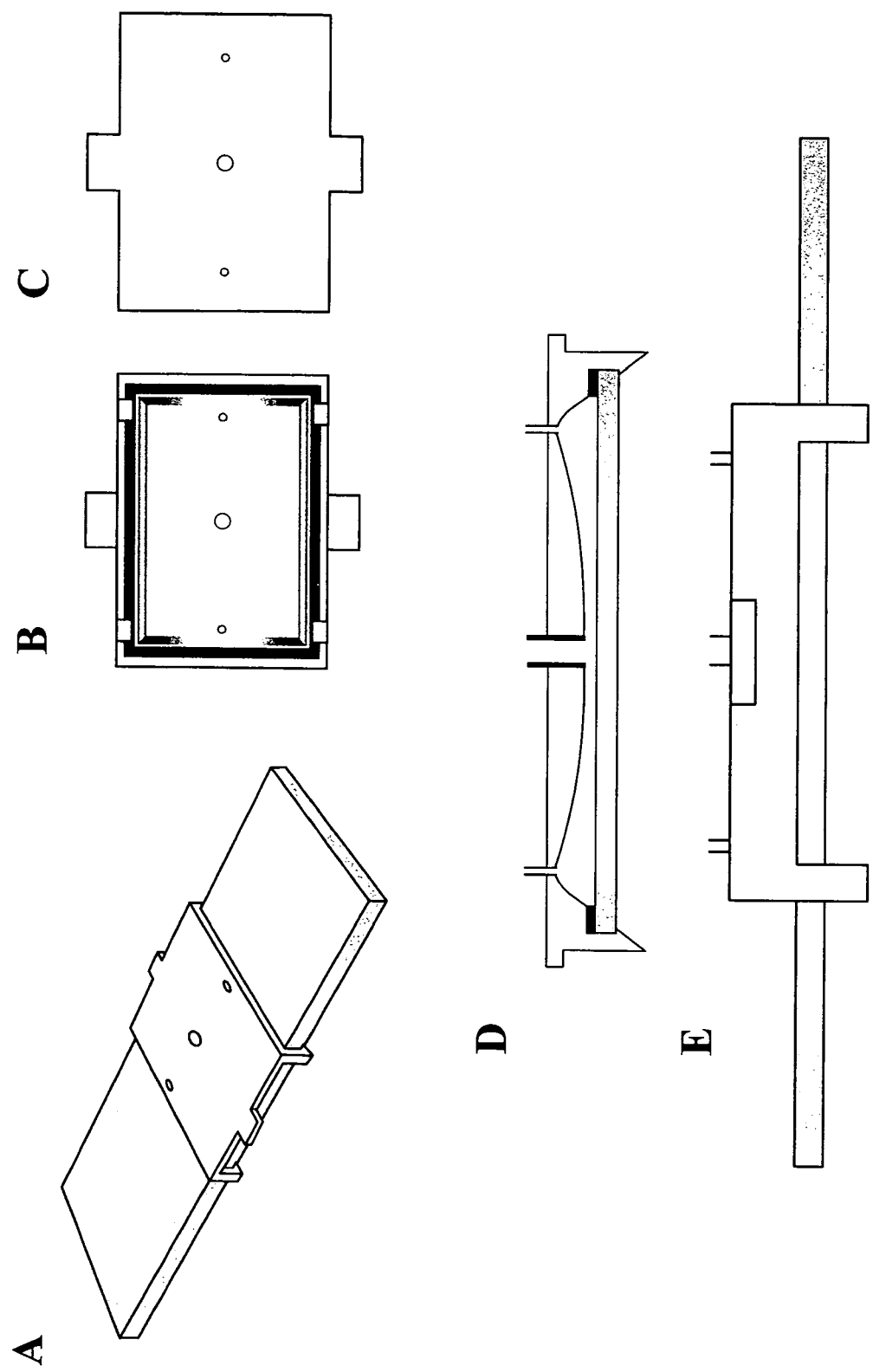
FIG. 2A is a perspective view of a combination of the base and the slide cover as shown in FIG. 1. The slide cover is adapted to clip onto the base.
FIG. 2B is a top plain view of the slide cover.
FIG. 2C is the bottom plain view of the slide cover.
FIG. 2D is the cross-section of the front view of the combined slide cover and base, showing that the central portion of the inner surface of the slide cover is protruded toward the base and the surrounding portion of the inner surface of the slide cover is recessed, so as to form a space between the top surface of the base and the inner surface of the slide cover, with the shallow area in the central portion and the deep area in the surrounding portion.
FIG. 2E is the front view of the slide cover and base combination.
Figure 3:
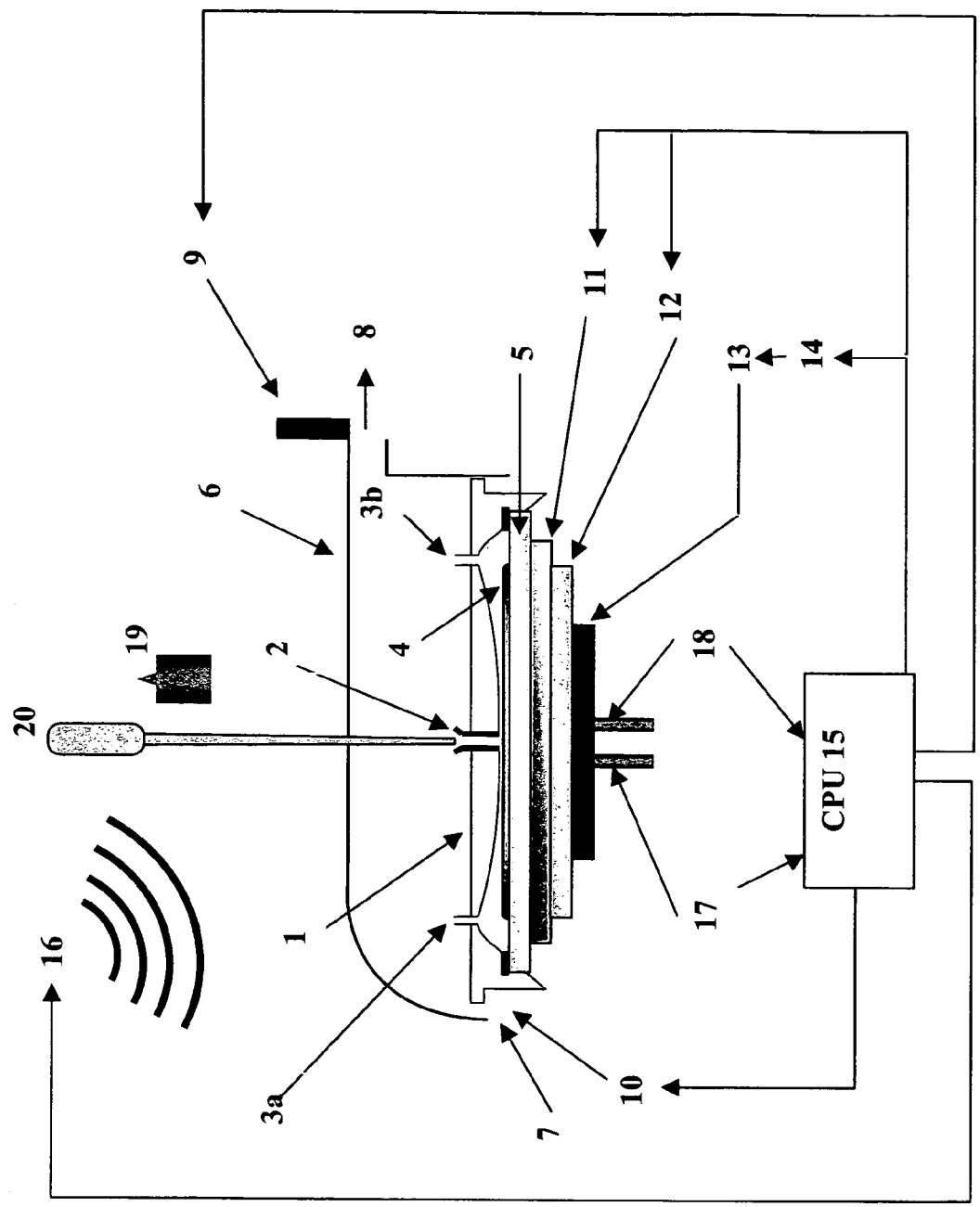
FIG. 3 is a cross-section of the front view of a preferred embodiment of the NDME device containing, as essential elements, a slide cover (1), a base (5), and a thermal control device. As shown in this Figure, the thermal control device can be a hot block (11); a cold block (12); an ultrasound transducer (13) which is controlled by an ultrasound generator (14); a CPU (15); a microwave generator (16), an ultrasound sensors (17), and/or a thermocouple (18). Any of the listed thermal control devices can be used individually or in combination of others. The slide cover has a central opening (2), and two lateral holes (3a, 3b). A cap (19) is added to the central opening (2) of the slide cover (1) to prevent the extraction solution from being dried up. A tissue specimen (4) is laid on top of the base (5). A chamber cover (6) has an inlet (7) for infusing steam, an outlet (8) for removing steam, a valve for controlling steam pressure (9), and a steam/humidity generator (10) for generating the steam. A pipette (20) is shown which demonstrates where the extraction solution is added to the space formed between the top surface of the base and the inner surface of the slide cover.

The NDME device can extract sufficient macromolecules for proteomic and genomic analysis from a single tissue section of 4-25 mm$^2$×5 μm without destroying the tissue morphology. A preferred embodiment of the NDME device is illustrated as follows, as shown in FIGS. 1-3, although variations are contemplated by skill artisans:

1. A base: the base (5), as shown in FIGS. 1-3 is designed to hold the tissue specimen and to be used as the central support for the rest of the parts of the device. The base (5) is preferred made of glass, plastic (such as polystyrene or polypropylene), TEFLON, silicon wafer, ceramic, or metal. The most preferred material is glass.

2. A slide cover: The slide cover (1), as shown in FIGS. 1-3, of the NDME device is specially designed to be able to clip onto the base and to provide a sealable environment for containment of the extraction solution. The slide cover (1) is preferably made of inert materials that do not interact with the tissue sections and/or the buffers/extracts. Examples of materials for the slide cover include, but not limited to, metal, glass, TEFLON, membranes, and polymeric material (such as polystyrene and/or polypropylene). As shown in FIG. 2B, the preferred slide cover has a rubber frame to form watertight extraction chamber with the base. As shown in FIG. 1, the central portion of the slide cover (1) is approximately 1-2 mm apart from the tissue section that is laid onto the base, and the edge of the slide cover (1) inside the rubber frame is dented away from the slide. This design allows capillary action to hold the extraction solution only over the central tissue section. As shown in FIGS. 1, 2(D), and 3, the slide cover has a central opening (2) for applying and retaking the extraction solution. Also, as shown in FIGS. 1, 2(A)-2(D), and 3, the slide cover (1) has two lateral small holes (3a, and 3b) in the dented edge, which is designed to let air in and out. The central opening (2) can be sealed with a cap (19) during extraction, but the two lateral holes (3a and 3b) are always open to balance the pressure during heating/cooling. The extraction chamber is preferred to hold 5-250 μL buffer, depending on the size and thickness of the tissue section. The slide cover (1) can also be completely sealed without any opening during the extraction.

3. A thermal control device: The NDME technology is based primarily on applying physical force, particularly by controlling the temperature and optionally humidity, at a prescribed period of time, to facilitate dissolution of soluble macromolecules. Thus, a thermal control device, such as a heat-cold steam cycler/generator, a hot block, a cold block, a thermocouple (18), would provide temperature control for accelerating the extraction process (FIG. 3). In addition, microwave provides an electromagnetic force which can induce intra-heating/agitation and ultrasound wave induces localized cavitations and extreme pressure/temperature, which are useful for facilitating protein dissolution, cell membrane permeability, and enzymatic activity inhibition (FIG. 3). The microwave is provided by a microwave generator (16). The ultrasound is provided by an ultrasound transducer (13) and a ultrasound generator (14), and is monitored by an ultrasound sensors (17).

The NDME device is preferred to operate in the temperature between −20° C. and 120° C. (high temperature: 120° C.-50° C.; medium: 50-15° C.; low: 15-1° C.; and frozen: 0-−20° C.).

In addition to the above-mentioned three main parts, the NDME device optionally contains a chamber cover (6), as shown in FIG. 3, which has one inlet (7) for infusing the steam and one outlet (8) for removing the steam. The chamber cover (6), in combination with its inlet (7) and outlet (8), controls wet/cold air/steam to the NDME device, which in turn allows rapid exchange of temperatures and controlling the humidity in the device. The steam or humid gas is provided by a steam/humidity generator (10). The chamber cover (6) further has a valve (9) for releasing steam pressure. The chamber formed by the chamber cover (6) is sealable, allowing entry/exit of steam/humid gas to rapidly change temperatures inside. The temperature is detected and controlled by a CPU (15).

The combined effect of the thermal control device and the chamber cover allows the NDME device to effectively perform the extraction process. In general, the NDME device operates at the low to mild temperatures (4-25° C.) for frozen samples, including frozen tissue sections, homogenized tissues, and/or cell cultures, although a wide range of temperature between −20° C. and 120° C. can be used. When high temperature is chosen, such as 100° C., it is preferred to extract the samples in a relatively short period of time, such as no more than 5 minutes. Exposing the frozen samples at high temperature for a longer period of time may destroy the integrity and morphology of the tissue samples. When the extraction process is conducted at frozen temperature (−20° C. to 0° C.), because this low temperature partly inhibits enzymatic activity and shows less impact on protein structure, a longer period of extraction time, such as 5 to 45 minutes, works just fine.

For fixed samples, particularly for formalin-fixed, paraffin-embedded (FFPE) tissue section, extraction is preferred to be conducted under a medium to high temperature, such as 50-100° C. The most favorable temperature for FFPE tissue specimens is at about 100° C. When the extraction is conducted at about 70-120° C., because such high temperature inhibits enzymatic activity and denatures proteins, it is preferred to infuse wet steam to the chamber to prevent the extracts and tissue specimens from being dehydrated. However, if a cap (19) is used to seal the central opening (2) and the two lateral holes (3a and 3b) of the slide cover (1) during the extraction process, dry air works just fine.

The extraction can be conducted under one fixed temperature throughout the entire extraction time, or under a temperature cycling. Heating-frozen-thaw (any range between −20 to 120° C.) cycling may help to break membranes of cell and/or microorganisms to release soluble proteins, DNA, and/or RNA. When moving between temperature settings, the change can be adjusted gradually or through direct switch on/off of hot/cold temperature controls.

In addition to temperature control, the extraction can be improved by changing the components in the extraction solution and by applying physical forces of various parameters, such as duration, intensity and frequency of ultrasound/microwave, and temperature. For example, RNA can be extracted under heating and ultrasonic condition when the sample contains low nucleic acid content tissue. Under high temperature condition, hydrophobic proteins, membrane proteins, and cytoplasmic proteins may be enriched.

The effectiveness and efficiency of the NDME system are also determined by the type of extraction solution used during the extraction process. Although any solution, including water, saline, and any commercially available buffer can more or less extract the biological molecules from the tissue specimens using the NDME device, the best performance derives from the use of a detergent in the solution. Without detergent in the extraction buffer is very difficult to adding or loading into the space between the slid cover (1) and the tissue section (4). Detergents, such as SDS, CHAPS, NP-40, Urea, Thiourea, sulphobetaines, tributyl phosphine, triton X-100, Tween 20 etc., are found suitable for this use. The preferred detergent is SDS, particularly used in conjunction with water. The preferred concentration of SDS is between 0.1 to 2% by weight and most favorably as about 0.5% SDS.

The NDME device of the present invention can avoid contamination use a individual chamber cover (6) for the individual slide samples, use minimum volume of buffers for maximum coverage of the tissue to achieve the highest concentration of extract, prevent liquid evaporation, allow rapid high or low temperature change, protect tissue morphology damage by physical force, and provide easy addition of buffers and removal of extracts.

The following examples are illustrative, but not limiting the scope of the present invention. Reasonable variations, such as those occur to reasonable artisan, can be made herein without departing from the scope of the present invention. Also in describing the invention, specific terminology is employed for the sake of clarity. However, the invention is not intended to be limited to the specific terminology so selected. It is to be understood that each specific element includes all technical equivalents which operate in a similar manner to accomplish a similar purpose.

EXAMPLE 1

The NDME Device

An NDME device was designed by Bio-Quick, Inc. (Silver Spring, Md.), which demonstrated good control of temperature and humidity, with optional implementation of ultrasound or microwave for improved extraction efficiency.

As shown in FIG. 3, the NDME device has a reaction chamber covered by a chamber cover (6), a snap-on slide cover (1) over a base (5). A thermal control device (e.g., a hot block (11); a cold block (12); an ultrasound transducer (13) controlled by an ultrasound generator (14); a microwave generator (16), an ultrasound sensors (17), and/or a thermocouple (18)) is adapted to connect to the bottom surface of the base (5) to provide physical forces (such as temperature and agitation) to the NDME device. The reaction chamber is formed between the chamber cover (6) and the slide cover (1). The reaction chamber has an inlet (7) for infusing steam into the reaction chamber and an outlet (8) for removing the steam from the reaction chamber.

The NDMB device uses an extraction solution to facilitate the dissolution of the biological molecules (such as proteins, DNA, and/or RNA) from the tissue specimens, as a chemical force for molecule extraction. The extraction solution is preferred to contain a detergent. Examples of the detergents that are suitable for use in NDME include, but are not limited to, SDS, CHAPS, NP-40, Urea, Thiourea, sulphobetaines, and tributyl phosphine,triton X-100, Tween 20. There are two preferred extraction solution especially useful in conjunction with the NDME method. One is the NDME-PE buffer, which contains water and about 0.5% SDS, which is especially effectively for protein/peptide extraction. The other is the NDME-NE buffer, which contains Triton X-100, EDTA, and optionally citrate (i.e., 0.01M citrate, 1 mM EDTA, 0.2% Triton X-100 in phosphate buffered saline) and RNA inhibitors.

Humidity and temperature, along with agitations, are controlled by the thermal control device and the reaction chamber. The slide cover (1), which can be securely mounted onto the base (5), is designed to hold a thin layer of an extraction solution over a tissue section. The slide cover has a central hole (2) to add and remove the extraction solution to and from the space formed between the base and the slide cover. The slide cover (1) also contains 2 lateral holes (3a and 3b) at the edges. After treatment with heating and cooling, the extraction solution can be removed from the space and ready for molecular analyses.

EXAMPLE 2

Sample Preparations

A. Materials and Methods

I. Tissue Selection and Preparation

FFPE tissues and frozen tissues from brain, breast, heart, pancreas, liver, lung, spleen, lymph node, colon, and prostate, were tested. The FFPE tissue sections spanned from 3-month old to 50-year old. Before the extraction, the FFPE sections were de-paraffinized by a 2-minute immersion in xylene for 5 rounds, 100% alcohol twice, 95% alcohol to rehydrate and then air-dried at room temperate for 5 minutes.

II. Protein and RNA Extraction

Tissue-PE LB buffer from Geno Technology, Inc. (St. Louis, Mo.), two commonly used antigen retrieval solutions with 1 mM EDTA and 0.01 M sodium citrate, and NDMB-PE (optimal for protein extraction), NDME-NE (optimal for nucleic acid extraction) and NDME-U (for protein and nucleic acid extraction) extraction buffers from Bio-Quick, Inc., Silver Spring, Md., were tested for extraction efficiency. Depending on the size of the tissue section, 5-250 μL of extraction buffer was added onto the deparaffinized slide section with a snap-on cover slip manufactured by Bio-Quick, Inc (Silver Spring, Md.).

As shown in FIG. 3, the tissue specimen was placed onto the base (5) in the NDME device (Bio-Quick, Inc., Example 1), covered with the slide cover (1). About 5 μl to 250 μl of the extraction solution was added to the space between the slide cover (1) and the base (5) through the central opening (2). The chamber cover (6) was connected to the NDME device. The thermal control device was turned on and heated to about 100° C. for 5 to 30 minutes while at the same time, wet steam was infused into the reaction chamber between the chamber cover (6) and the slide cover through the inlet (7) and removed from the outlet (8). After the completion of the reaction, the device was immediately cooled to 4° C. The extract was collected through the central opening (2) of the slide cover (1) and-used without further purification for gel-based protein analysis, PCR or stored at −70° C. for future use. For RNA analysis, the extract was treated with DNase I, denatured, reverse-transcribed into first strand cDNA, and then PCR amplified. After extraction, the slide was rinsed with PBS buffer for histological diagnosis such as H&E, IHC, CISH, and FISH studies. Alternatively, the slides were processed as normal FFPE slides for long-term storage.

III. IHC Staining

IHC staining carried out on tissue sections without the NDME treatment might require antigen retrieval according to conventional protocols. IHC staining carried out on tissue sections after the NDME treatment did not need any further antigen retrieval treatment. To block the endogenous peroxidase and unspecific protein binding, tissue sections were treated with 3% $H_2O_2$ for 10 min and 10% bovine serum albumin for 20 min at RT respectively before being incubated with antibodies against PAP, PSA, Her-2, ER, cyclin E, CEA, LCA, CD5, cytokeratin, CD20, CD30, and/or HIV p24 at various dilutions. After washed in PBS, all slides were incubated with either anti-mouse or anti-rabbit secondary antibody conjugated biotin at RT for half an hour. After washed in PBS, all slides were incubated with ABC kit for half an hour at RT. The development was then carried out with DAB substrate (Dako, Carpinteria, Calif.). Negative controls included staining without primary antibodies or use irrelevant primary antibodies.

IV. CISH and ISH Staining

ISH staining was carried out directly on slides after the NDME treatment. Fluorescein isothiocyanate (FITC)-labeled probes (BioGenex, San Ramon, Calif.) specific for MRNA of kappa and lambda immunoglobulin were applied to the tissue section, covered by a cover slip, and denatured at 100° C. for 5 minutes in a steamer. Tissue sections were allowed to cool down and hybridize with the probe at room temperature for about 1 hour. Tissue sections were washed twice, 3 minutes each, in 2×SSC, incubated for 30 minutes with monoclonal mouse anti-FITC, followed by two washes in PBS, 3 minute each. The tissue section was incubated with biotinylated secondary antibody for 30 minutes at room temperature followed by two 3-minute washes in PBS, and then incubated with streptavidin-biotinylated peroxidase for 30 minutes. After PBS washing, the slide was treated with 5-bromo-4-chloro-3-indolyl phosphate/nitroblue tetrazolium reagents for color development. Appropriate positive and negative controls provided by BioGenex were used with each reaction. C-Myc translocation CISH staining was performed according to the instruction from Zymed, Inc (South San Francisco, Calif.).

V. SDS-PAGE and Western Blot 1-5 μg of protein or 20 μL of extracts collected from the NDME device were mixed with SDS-PAGE loading buffer at a final concentration of 65 mM Tris, 5% 2-mercaptoethanol, 3% SDS, 10% glycerol, and bromophenol blue, denatured at 70° C. for 10 min, and applied to a 4-15% gradient NuPAGE gel (Invitrogen, Carlsbad, Calif.). After electrophoresis, the gel was removed and stained by silver staining or Coomassie blue according to the manufacture's instruction (Bio-Rad Laboratories, Hercules, Calif.) to visualize distribution of extracted macromolecules (proteins only for Coomassie staining and proteins and DNA/RNA for silver staining).

For Western blot analysis, the SDS-PAGE gel after separation was transferred onto a polyvinylidene difluoride (PVDF) membrane (from BIO-RAD) in transfer buffer containing 192 mM glycine, 25 mM Tris-HCl, pH8.3, 20% v/v methanol and 0.02% SDS at 100V for one hour. The membrane was washed once with TBS buffer (50 mM Tris-HCl, pH 7.5 and 150 mM NaCl) and blocked 1 hour to overnight in TBS buffer with 5% milk at RT with constant shaking. The membrane was then incubated with primary antibody at RT for 1 hour, washed three times with TTBS (TBS plus 0.1% Tween-20), incubated for 1 hour with peroxidase or alkaline phosphatase-conjugated anti-IgG antibody. After washing with TTBS three times, the membrane was treated with Lumi-GLO Elite or AP Color Development kits (KPL, Gaithersburg, Md.) to visualize protein bands.

VI. Reverse-Phase Protein Arrays

The proteomic analysis method previously described by Paweletz et al., *Oncogene.* 2001;20:1981-1989 was employed. Briefly, tissue extracts were arrayed onto nitrocellulose coated FAST slides (Schleicher and Schuell, Keene, N.H.). Each sample was spotted in a serial 1:2 dilution curve with duplicates of each dilution. Extraction buffer alone was spotted as a negative control. Slides were prepared for signal development by incubating for 10 minutes in a 10% solution of Mild Re-Blot Plus followed by incubation in I-Block, a casein-based blocking solution, for at least 1 hour. Signal was developed using the CSA system based on enzyme-mediated deposition of biotin-tyramide conjugates at the site of a biotinylated antibody-ligand complex. Arrays were analyzed with ImageQuant version 5.2 software (Molecular Dynamics, Amersham, UK). The spot intensity after background correction was proportional to the concentration of the target protein (Paweletz et al., *Oncogene.* 2001;20:1981-1989). Total protein was similarly determined after staining with Sypro Ruby, and was used to normalize for protein loading.

VII. SELDI-TOF MS

Proteins in the NDME extracts were purified and enriched using a hydrophobic reverse phase chip (H4) from Ciphergen Biosystems (Fremont, Calif.). The chip was prepared by placing 2 µL of acetonitrile to the spot and right before acetonitrile evaporated completely, 2 µL of protein extracts are applied to the surface. The chip was incubated at high humidity for 20 minutes to allow the protein sample to interact with the surface. After incubation, the chip was washed five times with 5 µL of 30% acetonitrile and allowed to air-dry. To each protein-bound chip spot, 1 µL of saturated sinapinic acid dissolved in 50% acetonitrile and 0.5% trifluoracetic acid was added to co-crystallize with the bound proteins. The chip was then transferred into the chip reader of the Protein Biology System 1 SELDI-TOF mass spectrometer (PBS-II) to measure the molecular weights of bound proteins according to an automated data collection protocol. Data interpretation is augmented by the use of the ProteinChip software v2.0.

VIII. RT-PCR Analysis of β-Actin mRNA Fragments

The cytoplasmic β-actin gene was chosen and amplified because this gene encodes for a structural protein that exists in all cells. Primers to generate different size amplicons ranging from 150 to over 1,000 bp were synthesized. PCR and RT-PCR were performed according to the Super Script III reverse Transcriptase and Taq Polymerase from Invitrogen (Carlsbad, Calif.). PCR reaction along with the appropriate controls usually underwent 30~40 amplification cycles. The PCR products were separated on a 2% agarose gel stained with ethidium bromide.

IX. Effect of the NDME Method on Tissue Morphology

Lymph node and prostate cancer FFPE tissue sections were extracted using the NDME method with NDME-NE and NDME-PE buffers for 20 minutes and high humidity heating at 100° C. Lymph node and prostate cancer frozen tissue sections were extracted using the NDME method with NDME-NE and NDME-PE buffers for 5 minutes and high humidity heating at 100° C. Morphologic study of both FFPE and frozen tissue sections after NDME treatment were performed using H&E staining. Extracted soluble proteins were analyzed on an SDS-PAGE.

X. Effect of Different NDME Buffers on Tissue Morphology and Antigenicity

Lymph node FFPE sections were extracted using the NDME method with NDME-NE or NDME-PE buffers. The tissue sections were stained with H&E and ICH.

XI. Study of Prion Disease by Simultaneous Morphological and Proteomic analyses Prion diseases also known as spongiform encephalopathies for their causing progressive degeneration of the central nerve system (CNS) result in vacuolar change, neuronal loss and gliosis in the cerebral cortex and cerebellum. Prion diseases are known to occur in both animals and humans. CJD (Creutzfeld-Jakob Disease) is the most common prion diseases that affect humans. Prion diseases in farm animals, e.g., sheep (scrapie) and cow (bovine spongiform encephalopathy) have the potential to cause major economic losses in the agricultural and food-related markets.

Prion stands for protein-based infectious disease. Prion protein has two conformational states: the normal 3 α-helix $PrP^C$ form and the disease-causing 2 α-helices, 1 β-sheet $PrP^{SC}$ form (c stands for cellular and sc stands for Scrapie). Proteinase K digests only $PrP^C$ but not $PrP^{SC}$, due to the conformational differences of these two forms of prion protein.

Normal brain and Prion brain tissue sections were treated with or without Proteinase K digestion. Then these sections were treated with the NDME method with NDME-PE extraction solution for 25 minutes and high humidity heating at 100° C. Extracted soluble proteins from normal and Prion cases were analyzed using Western blotting and the sections were analyzed using IHC staining. Both tests used specific Prion antibody (3F4) to determine the size and location of Prion proteins before and after proteinase K digestion.

XII. Cancer Diagnosis and Research

Because prostate cancer (PCa) is a hormone-responsive tumor, studies of the proteins regulating steroid metabolism in the prostate may shed light on the biology and clinical course of the disease. A broad-spectrum gene expression search recently identified alpha-methylacyl-CoA racemase (AMACR) as one of several proteins overexpressed in malignant prostate tissues. AMACR is an enzyme involved in the metabolism of branched long-chain fatty acids, which include intermediates of steroid hormone. AMACR is strongly and specifically positive in over 80% of prostate cancers, and its high sensitivity and specificity for PCa make it a promising PCa biomarker, despite that the biological function of AMACR in PCa development is not known.

The NDME method allows the analyses of proteins and nucleic acids from tissue extract without destroying the tissue so that a single tissue section (and microdissected section) can be used for molecule size-differentiation and identification using tissue extract while the tissue can be used for morphological and localization studies. This invention is the first to address the correlation of AMACR variants and PCa at both the molecular level (protein and mRNA) and at the morphological level using very small amount of tissues.

A blinded NDME study comparing protein expression patterns of frozen needle biopsy prostate specimens with PCa classification was conducted. Protein extracts were obtained from these specimens by NDME method and then compared to protein extracts obtained from cell lines, LNCap and 293. AMACR size and intensity were analyzed by Western blot with a polyclonal antibody (pAb) against AMACR from Abcam (Cambridge, Mass.).

XIII. Study of FFPE Prostate Cancer LCM Samples

NDME extract from 5-6,000 cells of neoplastic and benign epithelial prostate selected from FFPE tissue sections by laser capture microdissection (LCM) was collected and analyzed for AMACR by Western blot.

XIV. Study of Aged Tissue Section Samples

Smallpox is a highly contagious and virulent infectious disease caused by variola virus with a morbidity of 90% and morality of up to 30% in unvaccinated population. Vaccinia is a virus strain used for effective immunization against smallpox. Due to the eradication of endemic smallpox in 1980, vaccination ceased worldwide.

Though the whole genome of variola along with other poxvirus is available 10 years ago, virtually no data on authentic variola proteins are available. Recent development on detection of smallpox is mainly focused on variola DNA-based methods because of the simplicity and the availability of DNA identification techniques. Many real-time PCR procedures are developed for rapid identification of variola DNA using extracts from constructed recombinant plasmid or archived tissue samples. Virus DNA can also be distinguished directly on tissue sections by in situ hybridization. While PCR is faster and easier to perform, in situ hybridization also allows concomitant identification of the specific cells targeted by the virus.

Due to the unavailability of variola virus and the lack of study on variola proteins, no specific antibody against smallpox is present. The technology of NDME alone provides an effective way to extract proteins and RNA/DNA from archived tissue and to perform retrospect proteomics studies of many archived diseases, especial those that are not encountered in today, i.e. smallpox.

The NDME technique was applied to extract proteins and nucleic acids from a single slide section of 50-year old tissue sections of a smallpox patient and other archived sections and the controls: normal skin, vaccinia-infected tissue, herpes simplex virus-infected tissue. PCR and immunochemical stain were performed on the NDME extracts.

B. Results

1. NDME Extracted Both Proteins and Nucleic Acids from FFPE Tissues

Biological molecules extracted from FFPE tissue sections in various extraction buffers were compared using SDS-PAGE. In general, Coomassie blue staining detects protein, but not DNA/RNA, at the level of 0.3 to 1 μg/band, while silver staining detects both protein and DNA/RNA with a much higher sensitivity (2 ng/band).

Figure 4:
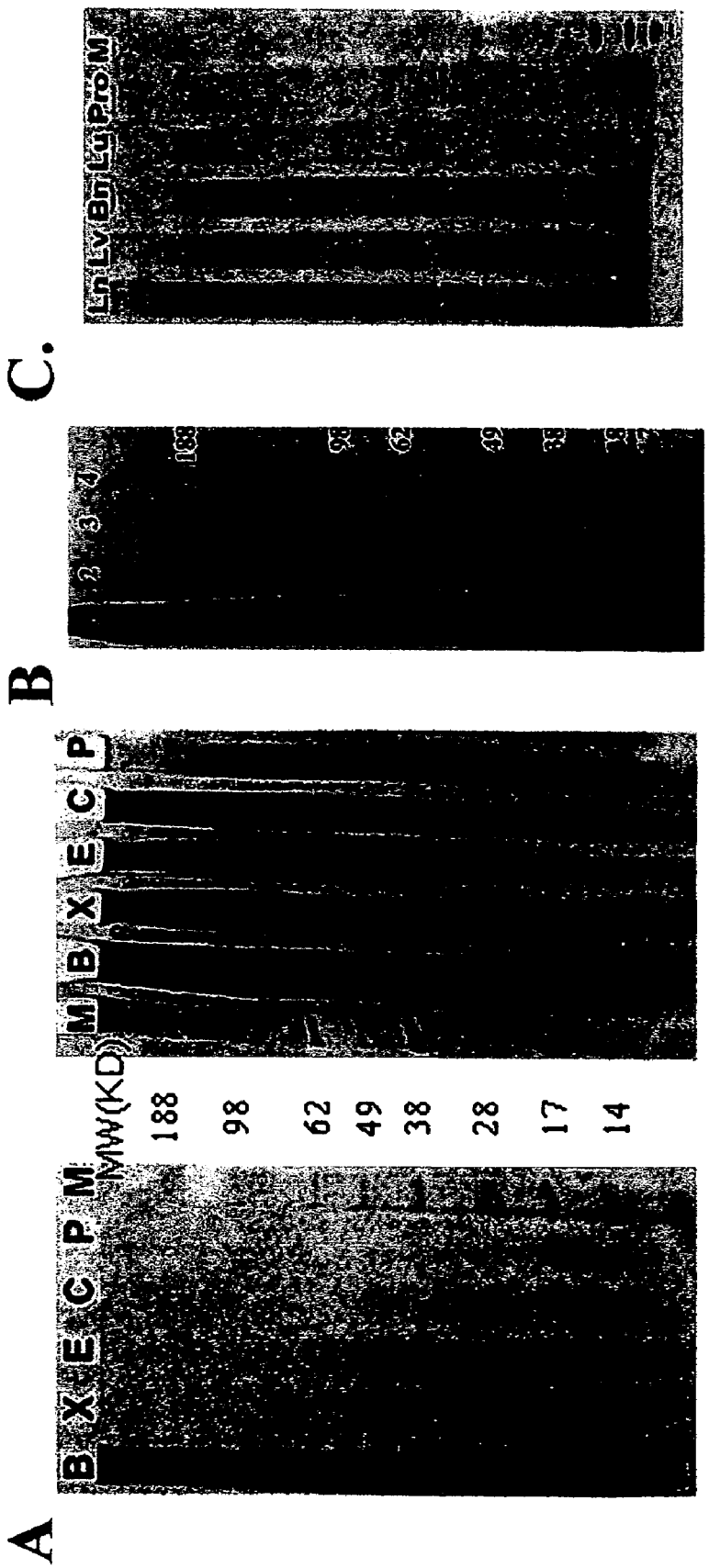
FIG. 4 shows Sodium Dodecyl Sulfate (SDS)-polyacrylamide gel electrophoresis (SDS-PAGE) analysis of proteins extracted from fresh or FFPE tissue sections by the NDME method using various buffers.

As shown in FIG. 4A, NDME-PE (Lane B) extracted a significantly greater amount of proteins than other buffers (lanes X, E, C, and P). A greater number of high MW species were observed with silver staining than with Coomassie blue staining, indicating the presence of a large amount of nucleic acids in the solution. The amount of proteins extracted from tissue sections were also affected, as expected, by whether the tissue was fresh or formalin fixed (FIG. 4B). Usually, about 5-10 μg total proteins and about 0.1-0.3 μg total nucleic acids were extracted from a typical fresh tissue section (5 μm×1 cm$^2$). The amount of macromolecules extracted from conventional FFPE tissues was about 10%-25% of that from fresh tissues. The experiment indicated that the NDME technique is able to extract both proteins and nucleic acids and suggested the possibility of selective extraction by modification of buffer components.

Proteins extracted from lymph node, liver, brain, lung, and prostate showed different band patterns (FIG. 4C), suggesting proteins of different types and quantities were extracted from FFPE tissue sections. The extracted proteins contained more low MW species than high MW species, but some proteins with MW as high as 188 KD were extracted, indicating that the NDME extraction method effectively reverses the cross-linkage between macromolecules and formaldehyde. Extending the extraction time would generate a relatively greater amount of high MW species at the expense of integrity loss due to destruction of the morphology of the tissue during prolonged extraction process.

2. Tissue Morphology Preserved After the NDME Treatment

What makes the NDME method unique as compared to other extraction methods is its ability to preserve tissue morphology after extraction treatment so that the same tissue section can be used for slide-based morphological and localization studies after extraction. H&E staining on tissue sections with the NDME treatment was usually brighter than that without the treatment as shown in FIG. 5A. Compared to the tissue section without the NDME treatment, lymph node section after the NDME treatment showed more eosinophoilic cytoplasm staining under the low magnification (100×) (data available). It seemed as if cell-cell space/gaps were disappeared, and cells and nuclear were slightly swollen so that nucleolus were more easily observed under high magnification (1,000×). Fine structures such as acidophilic granules, bibbed nucleus of eosinophils, the basophilic cytoplasm, and the rounded speckled chromatin nucleolus of plasma cell remained intact.

In addition to H&E staining, the NDME treatment enhanced IHC staining and removed the need for antigen retrieval. Using anti-CD5 antibody, immunohistochemical analysis was performed on consecutive FFPE tissue sections that had undergone the NDME extraction procedure for increasing lengths of time (FIG. 5B). Extraction solutions were analyzed on an SDS-PAGE gel (FIG. 5C). Without the NDME treatment (0 minute), the slide section revealed no visible IHC signal due to severe antigen masking after formalin fixation. Increasing the extraction time generated both greater intensity of IHC signals on the tissue section and higher amount of extracted molecules. A 5-minute incubation in NDME-PE generated few proteins. A greater amount of proteins, especially the higher MW species, was observed in extraction treatments exceeding 20 minutes. IHC signal increased with increasing length of extraction treatment up to 30 minutes, while tissue morphology remained largely unchanged up to 20 minutes. Detailed antigen location and morphology were clearly seen. There were noticeable morphologic changes after 30 minutes of extraction, as evidenced by the disappearance of blue hemotoxylin counterstaining in Panel A, probably due to the loss of nuclear structure. This experiment suggested that larger proteins might take longer to release because more cross-linkages needed to be reversed. In addition, proteins not at the cutting surface and proteins buried in membrane or cellular particles might need time to re-dissolve into solutions.

Also, as shown in FIG. 12, NDME treatment preserved the tissue morphology after extraction treatment, so that the same tissue section could be used for slide-based morphological and localization studies after extraction. H&E staining on the FFPE tissue section was typically more vivid on tissue sections treated with the NDME (FIG. 12(B)) than the untreated one (FIG. 12(A)). Cytoplasmic staining in sections of lymph node was also enhanced after the NDME extraction. Cell-cell space/gaps seemed to disappear, and individual cells and nuclei swelled slightly, making nucleoli easier to observe under high magnification (1,000×). Cytoplasmic structures, such as the eosinophilic granules of eosinophils, and nuclear features, such as the speckled chromatin pattern of a plasma cell nucleus, remained intact. H&E staining on the frozen tissue section was typically enhanced. Nuclear staining of tissue sections treated with the NDME (FIG. 12(D) showed better resolution than the untreated one (FIG. 12(C)).

H&E staining on tissue sections with the NDME treatment was usually brighter than that without the treatment (FIG. 13(A)). Compared to the different NDME buffers, lymph node FFPE tissue section after the NDME-PE treatment (FIG. 13(C)) showed more eosinophoilic cytoplasm staining under the high magnification (1,000×) than that treated with NDME-NE buffer (FIG. 13(B)). Cells and nuclear were slightly more swollen so that nucleolus and fine structures were disappeared by NDME-PE buffer extraction. However, acidophilic granules, bibbed nucleus of eosinophils, the basophilic cytoplasm, and the rounded speckled chromatin nucleolus of plasma cell remained intact.

Also, as shown in FIGS. 14 (14(A), (B) and (C), left panels), when various NDME buffers were used (A=control; B=with NDME-NE buffer; C=treated with NDME-PE buffer), lymph node H&E staining showed no difference staining under the low magnification (100×) (FIGS. 14(A), (B) and (C), left panels). However, IHC staining of Bcl-6 antigen (FIG. 14(A), center panel) showed negative staining on the section without the NDME treatment. NDME treated sections were positive (FIGS. 14(B) and (C), center panels). The NDME-PE buffer-treated tissue section (FIG. 14(C)) showed stronger staining than the NDME-NE buffer-treated tissue section (FIG. 14(B)). IHC staining of AMACR antigen on the prostate cancer tissue section, NDME-PE buffer-treated tissue section (FIG. 14(C), right panels) showed strong positive AMACR staining, but NDME-NE buffer-treated prostate cancer section (FIG. 14(B), right panel) still showed negative staining.

The results of FIGS. 13 and 14 confirmed that the NDME-PE buffer was more suitable for protein extraction. After the NDME, the morphology and antigenicity of the tissue sections were preserved, and could presented better contrast in staining with both H&E and IHC.

3. Analysis of Proteins in the NDME Extracts and On Tissue Sections After NDME Extraction To investigate whether proteins extracted by the NDME procedure retain their integrity (size) and antigenicity, proteins extracted from archived FFPE sections were separated by SDS-PAGE, transferred to PVDF membrane, and immunoblotted with 4 antibodies, as shown in FIG. 6. All 4 antibodies recognized their corresponding antigens at the expected size. In Panel A, anti-p24, an antibody specific for a 24 KD UHV capsid protein, detected a band in an HIV(+) lymph node, but not in an HIV(−) reactive lymph node (LN), while a 32 KD band corresponding to a general membrane glycoprotein was observed in the same extract from reactive LN by anti-CD20, as expected. In Panel B, anti-cyclin E detected a 52 KD common nuclear protein band in both extracts from tissues of anaplastic large cell lymphoma (ALCL) and Burkitt's lymphoma (BL). In contrast, anti-CD30 detected an 85 KD precursor protein processed in Golgi particles and a mature 120 KD protein in an ALCL section, as expected, but not in a BL section (Panel C). Molecular analysis (FIG. 6B) was well correlated with the IHC (FIG. 6C) on tissue sections after the NDME treatment, showing that ALCL expressed both cyclin E and CD30, while BL expressed only cyclin E. Large size membrane proteins such as 180 KD CEA and 220 KD LCA were extracted by NDME method (data available). This experiment also demonstrated that molecular analysis provides information on the size(s) and quantity of proteins, while IHC provides details of cellular morphology and the distribution of protein expression.

4. Protein Extracts Analyzed by Modern Techniques

A compelling reason to develop a non-destructive molecule extraction method is to combine classic pathological diagnosis with the more technologically advanced protein biochip techniques and protein profiling, such as protein arrays and SELDI-TOF MS (Fetsch et al., *Am J Clin Pathol.* 2002, 118(6):870-6). Proteins extracted from various tissues by the NDME procedure were 2-fold sequentially diluted with NDME-PE and applied onto nitrocellulose-coated glass slides to make reverse-phase protein lysate microarrays (FIG. 7). In comparison to the extract from frozen tissue (No.1), substantial amount of total proteins were extracted from either ethanol (No. 3) or formalin fixed (the rest) tissues. While common keratin proteins were observable in various tissue types, prostate-specific proteins PSA (prostate-specific antigen) and PAP (prostatic acid phosphatase) were almost exclusively expressed in all 3 prostate tissues (No. 8-No. 10).

FIG. 8 showed the SELDI-TOF MS spectra of proteins extracted from FFPE tissue sections by the NDME technique. Protein extracts from FFPE tissue sections were enriched and desalted by binding to a commercially available hydrophobic reverse phase protein chip and then the bound proteins were analyzed by SELDI-TOF MS. The overall profiles of proteins extracted from the FFPE tissue and the frozen tissue were clearly quite similar. This observation held true for the spread out spectra showing low mass/charge (m/z) range and 10K-21K high m/z range (FIG. 8A). Buffer components affected not only the type and the amount of molecules to be extracted from tissue section (FIG. 4), but also the binding affinity and selectivity of protein chip. That was why protein profiles were more heavily affected by the type of extraction buffer than by how the tissue is preserved. Although more systematic study might be needed to find the best buffer for fresh and differently fixed tissues so that the protein profiles could best resemble that of the fresh tissue, FIG. 8 indicated that the NDME technology was well suited to extract high quantity and full spectrum of proteins and was compatible with modern technologies for molecular analysis, such as protein arrays and mass spectrometry.

5. Sensitivity and Specificity of the NDME Technique

The NDME technique was of high efficiency. Enough proteins could be extracted from a tissue section of 3 mm$^2$ for less sensitive Western blot gel analysis. As shown in FIG. 9, FFPE tissue section after microdissection of the size of 1.5×2 mm$^2$ generated enough signal to show a specific ER band on Western blot, even though very little amount of total proteins were visible in comparison to other normal-sized sections. No ER band was detected for Case 2, which was ER-negative. The tissue sections were used for further morphological immunochemical evaluations after the NDME extraction. Case 1 was of Her-2(+) and ER(−) breast carcinoma, that except for a few normal glands, most glands were neoplastic and positive for Her-2 (FIG. 10C). The normal glands were ER positive and the neoplastic glands were ER negative. That was why on the Western blot the ER band of extract from Case 1 was not as strong as the one from Case 3ER(+) breast carcinoma. Furthermore, NDME extract from 5~6,000 cell of neoplastic and benign epithelial prostate selected by laser capture microdissection was able to detect PAS, PAP, and AMACR by Western blot (data are available). These results demonstrate that the NDME technology has high efficiency and specificity to allow selective protein analysis and profiling after microdissection.

6. Analysis of DNA/RNA in NDME Extracts and on Tissue Sections after Extraction

DNA and RNA of good quality and integrity were extracted by the NDME technology and directly adjunct to downstream PCR and RT-PCR amplification (FIG. 10). Quantitative study indicated that the amount of mRNA extracted from the FFPE tissue section was less than 50% of that from frozen tissue, depending on how well the RNA was preserved during the tissue fixation process. Using the NDME technique, extracts from a single section of 30-year-old archived FFPE retinal tissue generated RT-PCR products 367 bp long in 4 out of 6 samples (FIG. 10A). PCR products of 1,309 bp were similarly obtained from tissue extracts (FIG. 8C). Furthermore, as shown in FIGS. 10B and 10D, tissue sections after NDME treatment could be used for slide-based localization analysis, such as RNA-ISH (BioGenex, San Ramon, Calif.) and CISH (Zymed Inc., South San Francisco, Calif.). Following the NDME procedure, tissue sections could still provide sufficient morphologic detail and good hybridization signals. Blue staining (FIG. 10B) revealed the location of Epstein-Barr virus early RNA (EBER) on consecutive sections of lymph node with infectious mononucleosis. There was no detectable difference in hybridization pattern and intensity before and after NDME treatment, but there was a decrease in counterstaining intensity following NDME. Likewise, clear c-Myc translocation was obvious in Burkitt's lymphoma tissue sections before and after NDME.

7. Study of Prion Disease by Simultaneous Morphological and Proteomic Analyses

The NDME results of tissue sections of normal brain tissue, Prion case I and Prion case II The results are presented in FIGS. 15A, 15B, and 15C, respectively. Proteinase K resistance PrP$^{SC}$ were only observed in the Western blotting (center panels) and IHC staining (bottom panels) of prion disease cases (FIGS. 15B and 15C). The results demonstrated that the NDME technology preserved the morphology of the tissue sections while extracting sufficient amount of proteins for further proteomic analysis.

8. Cancer Diagnosis and Research

Four frozen needle biopsy specimens obtained during radical prostatectomy were analyzed. As shown in FIG. 16, specimens 3 and 5 showed similar histology, categorized as poorly differentiated tumor, while specimens 2 and 4 were similar and could be categorized as well differentiated tumor (FIG. 16B). Different AMACR expression patterns were observed in tissue extracts from these specimens, which seemed to correlate to some extend to PCa histology. Extracts from cases 2 and 4 showed two AMACR bands with a major at 38 kDa and a minor at 49 kDa, while that from cases 3 and 4 showed a major band at 49 kDa. Furthermore, benign (1) and cancerous (2) regions of the same specimen were dissected and proteins separately extracted from both regions. AMACR from benign region only showed a faint band at 49 kDa, different from AMACR expression in the cancerous B regions. Prostate cancer cell line LnCap showed the major band at 38 kDa while a human embryonic kidney cell line 293 showed two bands at 62 kDa and 170 kDa. These two high MW species were out of the range of the five possible AMACR variants with MW between 54-25 kDa. It was predicted that these species might be resulted from dimmerization and/or post-transcription modification.

It was evident that equipped with the NDME method, prostate tissue histology and AMACR protein expression patterns using a single slide section could be achieved.

9. Study of FFPE Prostate Cancer LCM Samples

As shown in FIG. 17, different AMACR sizes and strengths in extracts were observed between prostate cancer cases 1 & 2 and cases 3, 4 & 5. These results demonstrated that the NDME technology was efficient and specific enough to allow selective protein analysis and profiling after microdissection.

10. Study of Aged Tissue Section Samples

PCR products corresponding to the orthopoxvirus hemagglutinin gene products of 209 bp was amplified from the smallpox tissue (case 4) NDME extract and is presented in FIG. 18E. Real-time PCR products corresponding to the vaccina hemagglutinin gene product was amplified from the vaccinia-infected tissue (case 3) NDME extract and is presented in FIG. 18F. In addition, after the NDME treatment, the 50-year old smallpox-infected clinical section (case 1and 4) was positive when immunochemically stained with an anti-vaccinia antibody (FIG. 18B). The vaccinia-infected tissue (case 3) was a positive control and herpes simplex virus-infected tissue (case 5) and normal skin tissue were negative controls (case 2).

An anti-vaccinia antibody that recognizes different protein products in human skin tissues infected by smallpox virus from that by vaccinia virus was used. Like other antibodies raised against vaccinia virions, this anti-vaccinia polyclonal antibody cross-reacts with smallpox virus. However, it bound a single 65 kD protein in smallpox-infected tissue (cases 1 and 4) extract but a major 200 kD protein and a minor 65 kD protein in generalized vaccinia-infected tissue (case 3) extract (FIG. 18C). The housekeeper keratin proteins were reacted with anti-pan keratin antibody AE1/AE3 (FIG. 18D). Typical H&E morphologic features of cases 1, 3 and 4 consistent with the ballooning degeneration of the epidermal cells of the stratum spinosum resulted in intracellular swelling, intercellular edema, and ultimately cellular lysis leading to the formation of microvesicles (FIG. 18A).

It was evident that NDME was a useful tool for retrospect research study. NDME technique allowed not only the use of section extract for protein identification and PCR analysis, but also the use of the tissue section after molecule extraction for histopathological, immunochemical, and in situ hybridization studies.

C. Discussion

Examples described above demonstrated that NDME technology not only extracted enough soluble proteins, DNA, and RNA from a single fresh frozen or a FFPE tissue section for molecular detection, such as SDS-PAGE, Western blot, and RT-PCR, but also maintained the integrity of tissue morphology, protein antigenicity, and intact chromosomal structures after extraction. Thus, this technology provides a useful means to obtain and compare both histological and molecular diagnosis on a single tissue section.

It is commonly thought that FFPE tissues cannot be used for high throughput analysis such as biochip molecular profiling. However, it has been known for a long time that protein cross-linkage by formalin is reversible (Jackson, *Cell* 1978, 15(3):945-954) and that the cross-linking occurring during the process of formalin fixation retains the secondary structure present in fresh tissue (Mason et al., *J Histochem Cytochem.* 1991, 39(2):225-229). There are increasing evidences that formalin-induced macromolecule cross-linking can be reversed under high temperature (Mason et al., *J Histochem Cytochem*. 1991, 39(2):225-229). The inventor found that various methods including heating, microwave, and ultrasound were all able to reverse such cross-linking to some extend. With 20 minutes or so high humidity heating followed by immediate cooling, the NDME procedures described in this paper can reverse protein cross-linking in FFPE sections, releasing proteins for proteomic analysis. In contrast, adding extraction buffer to fresh frozen tissue section without heating or for a minimum of 5 minutes heating was able to release proteins and nucleici acids for SDS-PAGE and PCR amplification (FIGS. 4B, 5A and 10C). Protein extraction from fixed tissues requires three basic steps: reversal of protein cross-linking, solubilization of uncross-linked proteins into buffer, and stabilization of proteins in the buffer. It is hypothesized by the inventor, as depicted in FIG. 11, that the NDME process induces release of macromolecules from the exposed side of a tissue section that is immersed in extraction buffer. Implementation of microwave and ultrasound energy facilitates the reversion of cross-linking and the penetration of buffer into the tissue, allowing the release of dissolvable macromolecules into the buffer.

Many people question the possibility of molecule extraction from intact slide section, because all conventional extraction methods require homogenization of tissues, fresh or fixed. The inventor believes that the thickness of the tissue sections of 4-5 micron plays an important role to facilitate molecule extraction. According to basic histology, T lymphocyte is the smallest cell of about 6-7 micron in diameter. Tissue sectioning actually serves to cut through most of cells and exposes the cellular and nucleus contents to any contact solutions. The NDME procedures facilitate the reversion of cross-linking, help the release of proteins and nucleic acids, and stabilize released macromolecules in the extraction buffer. Thus, the composition of extraction has a great effect on the type and amount of molecules extracted. Several buffers that are optimized for either proteins, nucleic acids, or general purposes have been formulated by the inventor.

As demonstrated by the experimental results, the extraction duration, preservation method, temperature, and composition of the extraction buffer all have some impact on the quantity and quality of protein and nucleic acids extracted from frozen and fixed tissue sections using the NDME method. It was found that NDME-PE buffer was more efficient for protein extraction than NDME-NE buffer or other buffers, including common antigen retrieval buffers and one commercially available buffer. The composition of NDME buffer needs to be compatible with the downstream molecular analysis, such as SDS-PAGE, high-pressure liquid chromatography (HPLC), MS and protein-binding biochip arrays. Different applications may require different extraction conditions, requiring variation of the extraction buffer composition, or variation of the duration and/or intensity of the microwave or ultrasound treatments. Variation of these parameters may allow selective macromolecular release (data available). A lyses buffer is critical for disruption of bipolar lipid membrane of cells to free and solubilize proteins, and in addition, to prevent precipitation by stabilizing and denaturing proteins. Some types of reagents may enhance the solubility of hydrophobic proteins, but may interfere with subsequent electrophoresis or MS detection (data available).

The mechanisms of cross-linking reversal and antigen retrieval are not clearly understood. Elucidation of these mechanisms will be very helpful for optimization of macromolecular extraction. Current methods for antigen retrieval include proteinase pre-digestion (Huang, *Lab Invest*. 1975, 33(1):88-95), chemical pretreatment, and heat-induced epitope retrieval. In this invention, the inventor sought to maintain the original morphology of the tissue sections and to avoid damage to extracted proteins. Thus, because tissue integrity and antigenicity may be lost as the result of the enzymatic activity of proteinase K, the inventor excluded proteinase digestion as a method of antigen retrieval. Pretreatment in solutions containing formic acid or urea has been shown to improve antigen unmasking in IHC staining (Kitamoto et al., *Lab Invest*. 1987, 57(2):230-6; and Hausen et al., *Stain Technol*. 1982, 57(5):321-324). Shi et al further demonstrated that optimal antigen retrieval was enhanced by heating tissue sections with microwaves for 20 minutes (Shi et al., *J Histochem Cytochem*. 1991, 39(6):741-748). Lower temperatures required a much longer time to achieve the same result.

In the present invention, the NDME technology can process samples with the level of formalin fixation varied substantially from sample to sample as processing of surgical samples could not be adequately controlled. In routine practice, surgical tissue samples are fixed in formalin overnight and then processed with graded alcohol, xylene and paraffin for another 12 to 20 hours. But in some cases, tissues are left in formalin for as long as 48 hours. It is well known that antigen retrieval may be difficult in over-fixed samples even after prolonged pretreatment. In general, the longer the NDME procedure, the more macromolecules is released, and the more tissue morphology is deviated from its original features. Over-fixed tissue may require longer heating during the NDME procedure, while fresh tissue section does not need heating.

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A method for extracting biological molecules from a biological sample, comprising:
   a. placing the biological sample onto a flat surface of a base;
   b. mounting a slide cover onto said flat surface of said base to form a space between said flat surface of said base and the inner surface of said slide cover over said biological sample;
   c. adding an extraction solution to said space between said flat surface of said base and said inner surface of said slide cover, said extraction solution facilities the dissolution of a pre-determined biological molecule from the biological specimen;
   d. placing the above mentioned assembly containing said biological sample, said flat surface of said base, said slide cover, and said extraction solution in an incubation chamber;
   e. incubating at a temperature; and
   f. collecting said extraction solution which contains the biological molecules extracted from said biological sample for downstream assays.

2. The method according to claim 1, further comprising infusing steam into said incubation chamber to maintain temperature and humidity within said incubation chamber.

3. The method according to claim 1, wherein said biological sample is a thin-section of a frozen tissue, a cytological smear, or a thin layer of microorganisms or cultured cells.

4. The method according to claim 1, wherein said biological sample is a paraffin-embedded tissue section, and wherein a step of deparaffinization is inserted between step a and step b.

5. The method according to claim 1 wherein said incubation temperature is between −20.degree. C. to 120.degree. C.

6. The method according to claim 5, wherein said incubation temperature is between 4.degree. C. to 100.degree. C.

7. The method according to claim 6, wherein said biological molecules are extracted from said biological sample in about 5 minutes to 120 minutes.

8. The method according to claim 1, wherein said extraction solution contains a detergent.

9. The method according to claim 8, wherein said detergent is 0.01% to 5% by weight of sodium dodecyl sulfate (SDS).

10. The method according to claim 9, wherein said SDS is at 0.1% to 2% by weight.

11. The method according to claim 9, wherein said extraction solution is for protein and/or peptide extraction.

12. The method according to claim 8, further comprising ethylenediaminetetraacetic acid (EDTA).

13. The method according to claim 12, wherein said extraction solution is for nucleic acid extraction.

14. The method according to claim 1, wherein 5 .mu.l to 250 .mu.l of said extraction solution is added to said space between said flat surface of said base and said inner surface of said slide cover.

15. The method according to claim 1, wherein said biological sample is applied to histopathological staining after said biological molecules of said biological sample have been extracted.

16. A method according to claim 1, wherein said base is a microscopic slide.

17. A method according to claim 1, wherein:
said slide cover has a center opening for adding and retrieving said extraction solution and at least one lateral hole for releasing air;
the inner surface of said slide cover protrudes toward said flat surface of said base at the central portion of said slide cover; and
said space formed between said flat surface of said base and said inner surface of said slide cover is shallow around said central hole to facilitate retrieval of said extraction solution.

18. A method for extracting biological molecules from a biological sample, comprising:
placing the biological sample onto a flat surface of a base;
adding 5 .mu.l to 250 .mu.l of an extraction solution to said biological sample on said flat surface of said base, said extraction solution facilities the dissolution of a predetermined biological molecule from the biological specimen;
mounting a slide cover onto said flat surface of said base to form a space between said flat surface of said base and the inner surface of said slide cover over said biological sample;
placing the above mentioned assembly containing said biological sample, said flat surface of said base, said slide cover, and said extraction solution in an incubation chamber;
incubating at a temperature; and
collecting said extraction solution which contains the biological molecules extracted from said biological sample.

* * * * *